(12) United States Patent
Urich

(10) Patent No.: US 11,191,669 B2
(45) Date of Patent: Dec. 7, 2021

(54) TAPERED STRUCTURE IN A PHACOEMULSIFICATION DEVICE FOR NODE PLACEMENT

(71) Applicant: Johnson & Johnson Surgical Vision, Inc., Santa Ana, CA (US)

(72) Inventor: Alex Urich, Cota de Caza, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

(21) Appl. No.: 17/094,426

(22) Filed: Nov. 10, 2020

(65) Prior Publication Data
US 2021/0052422 A1    Feb. 25, 2021

Related U.S. Application Data

(63) Continuation of application No. 16/821,051, filed on Mar. 17, 2020, which is a continuation-in-part of (Continued)

(51) Int. Cl.
*A61F 9/007* (2006.01)
*A61M 1/00* (2006.01)

(52) U.S. Cl.
CPC ......... *A61F 9/00745* (2013.01); *A61M 1/774* (2021.05); *A61M 1/84* (2021.05); *A61M 2210/0612* (2013.01)

(58) Field of Classification Search
CPC ........ A61F 9/00745; A61F 2250/0095; A61M 1/0064; A61M 2210/0612;
(Continued)

(56) References Cited

U.S. PATENT DOCUMENTS 3,857,387 A    12/1974    Shock
3,941,122 A     3/1976    Jones
(Continued)

FOREIGN PATENT DOCUMENTS

CN    104055621 B    3/2017
EP      1212021 B1    9/2006
(Continued)

*Primary Examiner* — Phong Son H Dang
(74) *Attorney, Agent, or Firm* — Johnson & Johnson Surgical Vision, Inc.

(57) ABSTRACT

Disclosed is a surgical instrument directed to phacoemulsification for cataract eye surgery. The instrument generally includes a hollow titanium needle extending from a vibration generating handpiece. Together, the hollow needle and handpiece form an aspiration pathway to suck cataractous debris from an eye. A piezoelectric transducer in the handpiece generates both high and low ultrasonic frequency vibrations that rings the needle. The low frequency produces a node-free standing wave along the needle and the high frequency produces a standing wave along the needle with a node of minimum amplitude along the needle. Both frequencies produce a high anti-node at the needle's tip. The low frequency causes higher cavitation for emulsifying the cataract and the high frequency facilitates fragmentation of the cataract with a low heat portion of the needle at the eye incision point. The placement of the node along the needle can be tailored by way of a tapered section in a step horn region of the handpiece.

26 Claims, 14 Drawing Sheets

Related U.S. Application Data application No. 14/517,798, filed on Oct. 17, 2014, now Pat. No. 10,596,033, which is a continuation-in-part of application No. 13/430,633, filed on Mar. 26, 2012, now Pat. No. 9,216,035.

(58) Field of Classification Search
CPC ...... A61M 2202/0014; A61M 2202/09; A61B 2017/00146; A61B 2017/22018; A61B 2017/320084
See application file for complete search history.

(56) References Cited

U.S. PATENT DOCUMENTS

| | | | |
|---|---|---|---|
| 3,990,452 A * | 11/1976 | Murry | A61B 17/22012 606/169 |
| 4,428,748 A | 1/1984 | Peyman et al. | |
| 4,864,547 A | 9/1989 | Krsna | |
| 4,868,445 A | 9/1989 | Wand | |
| 4,989,588 A | 2/1991 | Kubota et al. | |
| 5,001,649 A | 3/1991 | Lo et al. | |
| 5,062,827 A | 11/1991 | Wiksell | |
| 5,112,300 A * | 5/1992 | Ureche | A61F 9/00745 310/323.18 |
| 5,123,903 A | 6/1992 | Quaid et al. | |
| 5,171,387 A | 12/1992 | Wuchinich | |
| 5,176,677 A | 1/1993 | Wuchinich | |
| 5,180,363 A * | 1/1993 | Idemoto | B06B 3/00 604/22 |
| 5,213,569 A | 5/1993 | Davis | |
| 5,255,669 A | 10/1993 | Kubota et al. | |
| 5,261,922 A * | 11/1993 | Hood | A61B 17/320068 606/167 |
| 5,269,297 A | 12/1993 | Weng et al. | |
| 5,276,376 A | 1/1994 | Puskas | |
| 5,346,469 A | 9/1994 | Ikeda et al. | |
| 5,387,180 A | 2/1995 | Lehmer | |
| 5,388,569 A | 2/1995 | Kepley | |
| 5,391,144 A | 2/1995 | Sakurai et al. | |
| 5,431,664 A | 7/1995 | Ureche et al. | |
| 5,630,420 A | 5/1997 | Vaitekunas | |
| 5,695,510 A * | 12/1997 | Hood | A61B 17/320068 606/169 |
| 5,897,569 A | 4/1999 | Kellogg et al. | |
| 5,938,677 A | 8/1999 | Boukhny et al. | |
| 6,319,220 B1 | 11/2001 | Bylsma | |
| 6,433,464 B2 | 8/2002 | Jones | |
| 6,733,451 B2 * | 5/2004 | Rabiner | A61B 17/22012 600/439 |
| 6,884,252 B1 | 4/2005 | Urich et al. | |
| 6,955,680 B2 | 10/2005 | Satou et al. | |
| 6,984,220 B2 | 1/2006 | Wuchinich | |
| 7,083,589 B2 | 8/2006 | Banko et al. | |
| 7,273,483 B2 | 9/2007 | Wiener et al. | |
| 7,431,728 B2 | 10/2008 | Gerry et al. | |
| 7,794,414 B2 * | 9/2010 | Rabiner | A61B 17/22012 601/2 |
| 7,876,025 B2 | 1/2011 | Ma et al. | |
| 8,009,508 B2 | 8/2011 | Young et al. | |
| 8,277,462 B2 | 10/2012 | Heymann et al. | |
| 8,303,530 B2 | 11/2012 | Injev et al. | |
| 8,303,613 B2 | 11/2012 | Crandall et al. | |
| 8,439,938 B2 | 5/2013 | Moore, Jr. | |
| 8,512,325 B2 | 8/2013 | Mathonnet | |
| 8,652,073 B2 | 2/2014 | Romano et al. | |
| 9,060,776 B2 | 6/2015 | Yates et al. | |
| 9,173,672 B2 | 11/2015 | Young et al. | |
| 9,283,113 B2 | 3/2016 | Chon et al. | |
| 9,339,284 B2 | 5/2016 | Du et al. | |
| 9,504,471 B2 | 11/2016 | Vaitekunas et al. | |
| 9,572,711 B2 | 2/2017 | Raney et al. | |
| 9,622,749 B2 | 4/2017 | Vaitekunas et al. | |
| 9,623,237 B2 | 4/2017 | Turner et al. | |
| 9,693,897 B2 | 7/2017 | Vezzu | |
| 10,052,120 B2 | 8/2018 | Du et al. | |
| 10,194,972 B2 | 2/2019 | Yates et al. | |
| 10,194,973 B2 | 2/2019 | Wiener et al. | |
| 10,263,171 B2 | 4/2019 | Wiener et al. | |
| 10,265,117 B2 | 4/2019 | Wiener et al. | |
| 10,278,861 B2 | 5/2019 | Bourne | |
| 10,470,788 B2 | 11/2019 | Sinelnikov | |
| 10,631,909 B2 | 4/2020 | Eichler | |
| 2002/0099400 A1 | 7/2002 | Wolf et al. | |
| 2005/0187514 A1 | 8/2005 | Rabiner et al. | |
| 2005/0234473 A1 * | 10/2005 | Zacharias | A61F 9/00745 606/107 |
| 2006/0235306 A1 * | 10/2006 | Cotter | A61B 17/1688 600/459 |
| 2007/0249941 A1 | 10/2007 | Salehi et al. | |
| 2007/0249942 A1 | 10/2007 | Salehi et al. | |
| 2008/0294087 A1 * | 11/2008 | Steen | A61F 9/00745 604/22 |
| 2009/0069712 A1 * | 3/2009 | Mulvihill | A61B 17/3415 600/564 |
| 2009/0143796 A1 | 6/2009 | Stulen et al. | |
| 2010/0069825 A1 * | 3/2010 | Raney | A61F 9/00745 604/22 |
| 2012/0302941 A1 | 11/2012 | Teodorescu et al. | |
| 2015/0045806 A1 | 2/2015 | Urich et al. | |
| 2016/0175150 A1 | 6/2016 | Banko | |
| 2017/0087014 A1 | 3/2017 | Potter, Jr. et al. | |
| 2019/0133822 A1 | 5/2019 | Banko | |
| 2019/0336161 A1 | 11/2019 | Scheller et al. | |
| 2020/0107848 A1 | 4/2020 | Apperson et al. | |

FOREIGN PATENT DOCUMENTS

| | | |
|---|---|---|
| EP | 1215881 B1 | 4/2009 |
| EP | 2760399 B1 | 12/2016 |
| WO | 0124716 A1 | 4/2001 |

* cited by examiner

TAPERED STRUCTURE IN A PHACOEMULSIFICATION DEVICE FOR NODE PLACEMENT

CROSS-REFERENCE TO RELATED APPLICATIONS

This application is a Continuation Application claiming the priority to and the benefit of U.S. patent application Ser. No. 16/821,051 entitled TAPERED STRUCTURE IN A PHACOEMULSIFICATION DEVICE FOR NODE PLACEMENT filed on Mar. 17, 2020, which is a Continuation-In-Part Application claiming the priority to and the benefit of U.S. patent application Ser. No. 14/517,798, now U.S. Pat. No. 10,596,033, entitle PHACOEMULSIFICATION ULTRASONIC DEVICE SWITCHING BETWEEN DIFFERENT OPERATIONAL MODES, filed on Oct. 17, 2014, which is a Continuation-In-Part Application claiming the priority to and the benefit of U.S. patent application Ser. No. 13/430,633, now U.S. Pat. No. 9,216,035 entitled SURGICAL INSTRUMENT RINGING A TITANIUM NEEDLE WITH A NODE OF MINIMUM AMPLITUDE IN A SUBSTANTIALLY CYLINDRICAL PORTION OF THE NEEDLE, filed on Mar. 26, 2012.

FIELD OF THE INVENTION

The present invention relates generally to the field of medical devices used in surgery, and more particularly to tools and methods used in phacoemulsification procedures.

BACKGROUND

Needles that are actuated at ultrasonic frequencies may be used in various contemporary surgical procedures. For example, the lens of a human eye may develop a cataracteous condition that affects a patient's vision. Cataracteous lenses are sometimes removed and replaced in a procedure commonly referred to as phacoemulsification. Phacoemulsification procedures are typically performed with a handpiece that actuates a needle at ultrasonic frequencies. The needle is inserted through an incision in the cornea up to a desired insertion depth, and then ultrasonic actuation at a specific frequency is used to break the lens within the lens capsule of the eye. The broken lens may be removed through an aspiration line that is coupled to the hand piece, drawing irrigation fluid and aspirated tissue from a hollow passage through the needle. It is to improvements in ultrasonic actuation of a phacoemulsification needle that embodiments of the present invention are directed.

SUMMARY

The present invention is directed to embodiments of a phacoemulsification device that can switch between above 60 kHz and below 60 kHz. The two frequencies produce different surgical effects when used to emulsify a cataracteous lens.

Certain embodiments of the present invention can therefore comprise an apparatus and methods directed to a surgical instrument to accomplish phacoemulsification are disclosed. The surgical instrument generally surgical instrument for a phacoemulsification procedure, the surgical instrument comprising: a handpiece that includes a piezoelectric transducer; a hollow titanium needle having a free distal tip and a supported end structure that is attached to the handpiece, the supported end structure includes external threads that mate with internal threads in the handpiece, the hollow titanium needle having a substantially cylindrical portion extending from the free distal tip towards the handpiece. a tapered section between the transducer and the substantially cylindrical portion of the needle; and the piezoelectric transducer configured to periodically vibrate the hollow titanium needle at either a low mode or a high mode, the substantially cylindrical portion devoid of a node of minimum amplitude at the low mode and the substantially cylindrical portion possessing a single node of minimum amplitude at the high mode.

Other embodiments of the present invention can therefore comprise a method to drive oscillations in a surgical instrument during phacoemulsification, the method comprising: providing a handpiece that includes a piezoelectric transducer, the handpiece possessing a tapered section that tapers towards a distal handpiece end, a hollow titanium needle having a free distal tip and a supported end structure that is attached to the distal handpiece end, the hollow titanium needle possessing a length being defined along a longitudinal axis of the hollow titanium needle; energizing the piezoelectric transducer to periodically longitudinally expand and contract in at least two ultrasonic driving frequencies that rings the hollow titanium needle 106 with at least either a high ultrasonic standing wave or a low ultrasonic standing wave; inserting the hollow titanium needle in an eye; and after the inserting step, energizing the piezoelectric transducer to drive the hollow titanium needle at either the high ultrasonic standing wave or the low ultrasonic standing wave, only the high ultrasonic standing possessing a node of minimum amplitude along the length of the hollow titanium needle.

Yes other embodiments of the present invention can therefore comprise a surgical instrument comprising: a phacoemulsification device possessing a handpiece that tapers to a tapered end, a hollow titanium needle attached to the tapered end, the hollow titanium needle having a substantially cylindrical portion that extends from approximately the tapered end to a free distal tip; and a transducer configured to drive the hollow titanium needle with either a low ultrasonic standing wave or a high ultrasonic standing wave, the high ultrasonic standing wave having a single node of minimum amplitude along the hollow titanium needle, the low ultrasonic standing wave devoid of any node of minimum amplitude along the hollow titanium needle.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving eye surgery.

Figure 1:
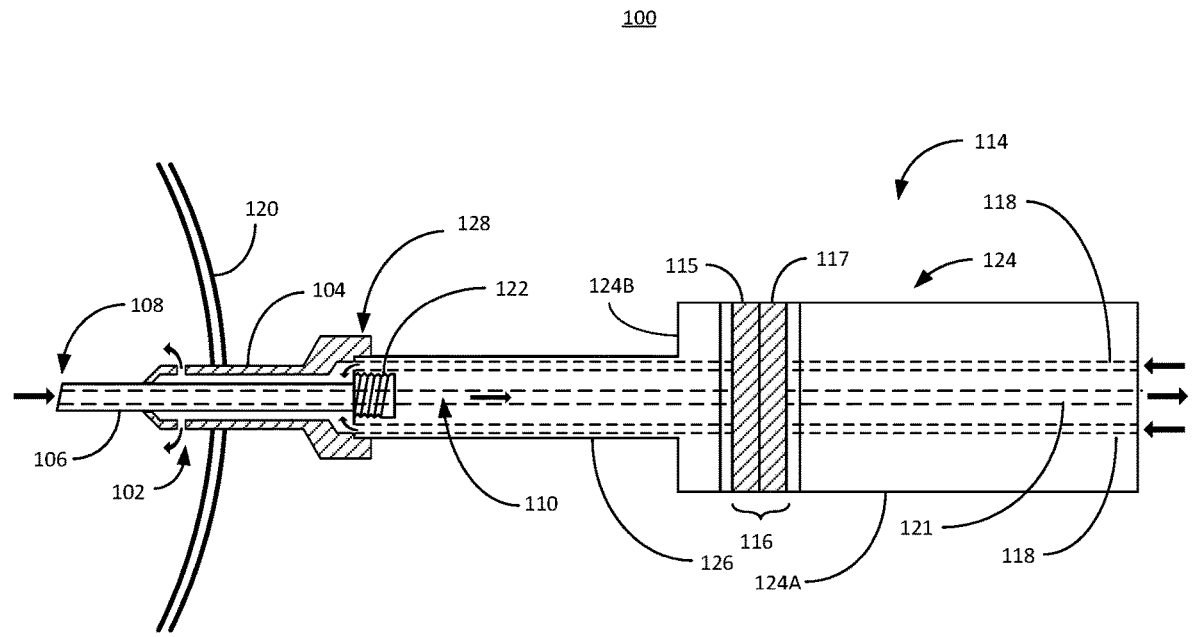
FIG. 1 illustratively depicts a line drawing of an embodiment of a phacoemulsification device inserted in an eye consistent with embodiments of the present invention.

To illustrate an exemplary environment in which preferred embodiments of the present invention can be practiced, FIG. 1 depicts an embodiment of a phacoemulsification device 100 inserted in an eye 120 consistent with embodiments of the present invention. As depicted, the phacoemulsification device 100 generally comprises a handpiece 114, a hollow aspiration needle 106 extending from the handpiece 114, an irrigation sleeve 104 that surrounds a portion of the aspiration needle 106 (also known as a phacoemulsification needle), and at least one irrigation port 102 extending through the irrigation sleeve 104.

During an ultrasonic phacoemulsification surgical procedure, a cataracteous lens may be broken into particles by the combined cutting action of an ultrasonically vibrating needle tip 108 and cavitation effects. The vibration may provide penetration of the needle 106 into lens tissue, while the cavitation may help emulsify or disintegrate lens tissue into small particles that can be aspirated through a narrow tube 110 in the hollow aspiration needle 106. Cavitation can occur because the hollow phacoemulsification needle 106 compresses and expands along its longitudinal axis, thus generating longitudinal waves in the surrounding fluid. Unlike torsional and shear waves, longitudinal waves may propagate well in fluids.

As further depicted in FIG. 1, the handpiece 114 includes a back cylinder 124 and a front cylinder 126, a piezoelectric transducer 116/124 comprising a pair of piezoelectric crystals 115 and 117 connected through a central bolt (not shown), irrigation pathways 118 and an aspiration pathway 121. The piezoelectric transducer comprises the back cylinder 124 (124A and 124B) and piezoelectric crystals 116 (the back cylinder 124 including a rear portion 124A and a front portion 124B, collectively 124). The hollow titanium needle 106 is attached to the handpiece 114 at the supported end 128. The supported end 128 generally comprises a supported end structure 122 that includes external threads that mate with internal threads in the handpiece 114. The hollow titanium needle 106 possesses a substantially cylindrical portion between the supported end structure 122 and the free distal tip 108. Substantially cylindrical defined herein is that the needle may not be a perfect cylinder, but rather may be something between a cylinder to a slight taper with the diameter of the needle at the supported end structure 122 being larger than at the needle free distal tip 108. Moreover, the needle may not be perfectly circular.

One embodiment of the handpiece 114 contemplates the back cylinder 124 possessing an outer diameter that is preferably in the range 9.5 mm to 13 mm. The back cylinder 124 may be generally comprised of stainless steel, for example. The handpiece 114 may also optionally include a front cylinder 126 that may have a front cylinder outer diameter that is preferably in the range 3.5 mm to 6.5 mm. In this case, the piezoelectric transducer 116/124 is preferably disposed between the back cylinder 124 and the front cylinder 126.

Figure 2:
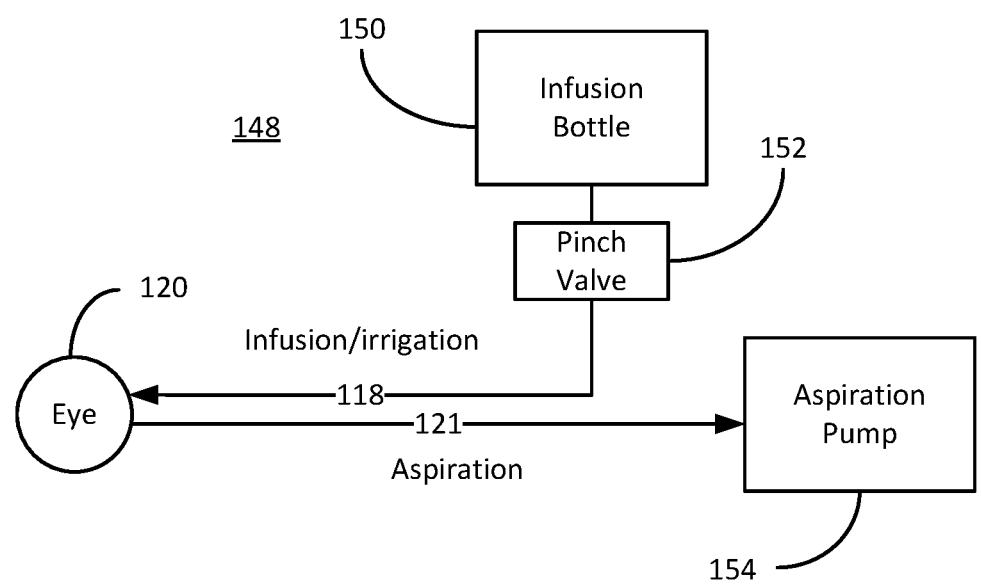
FIG. 2 is a block diagram of a phacoemulsification system embodiment consistent with embodiments of the present invention.

With reference to FIG. 2 in conjunction with FIG. 1, shown therein is a block diagram of a phacoemulsification system embodiment 148. As shown, the phacoemulsification system 148 includes an infusion bottle 150 of balanced salt solution generally positioned between 100 cm to 130 cm above the eye 120 (or to a level that gravitationally provides balanced intraocular pressure (TOP) in the eye 120, which is generally between 10 mm Hg and 20 mm Hg and averages to 15.5 mm Hg in a human eye. During a cataract surgery, a surgeon tries to keep the IOP above 20 mm Hg, especially after a vacuum surge. Osmotically balanced salt solution is compatible with the ocular fluid in the eye 120. The system 148 further provides a pinch valve 152 that opens and closes an infusion/irrigation pathway 118 to the eye 120. An aspiration pump 154 is adapted to suck emulsified lens material (ocular material) from the eye 120 through the hollow opening in the distal tip 108 of the hollow titanium needle 106. During a phacoemulsification procedure, the aspiration needle 106 is inserted through an incision in the anterior chamber of the eye 120 (at the cornea) up to and including the irrigation port 102. One embodiment contemplates the hollow titanium needle 106 vibrated at an ultrasonic frequency or at a high ultrasonic frequency to break up (emulsify) lens material in the eye 106. Ultrasonic frequency used herein is defined to be a frequency kHz below 60 kHz, and high ultrasonic frequency is defined to be a frequency above 60 kHz. The small pieces of the emulsified lens material are sucked through the hollow aspiration needle 106 away from the eye 120 along the aspiration pathway 121 by way of a vacuum generated by the aspiration pump 154. The aspiration pump 154 is adapted to pull (vacuum) a volume of emulsified lens material at a particular rate from the eye 120. Generally, the aspiration rate is approximately 25 to 50 cc of fluid/minute. Irrigation fluid replaces the removed lens material (at the same particular rate of aspirated lens material) by way of gravity from the infusion bottle 150 that is raised at an appropriate distance above the eye 120 to maintain IOP. The irrigation fluid flows (is discharged) into the inside of the eye 120 through the irrigation port 102 that is inside of the eye 120. In other words, the irrigation fluid replaces the lens material at the rate at which the lens material is removed from the eye 120 to maintain appropriate IOP, thus avoiding collapse of the anterior chamber of the eye 120. Hence, the irrigation flow rate into the eye 120 essentially equals the aspiration flow rate from the eye 120. The word essentially is used here to indicate that at some level there flow rate is not exactly equal, but for all intents and purposes is more or less equal. The irrigation port 102 is a pathway into the irrigation sleeve 104, whereby irrigation fluid passes from the irrigation sleeve 104 out the irrigation port 102 into the eye 120. The irrigation sleeve 104 is spaced apart from the hollow titanium needle 106 to form an irrigation pathway 118. The irrigation pathway 118 extends from the infusion bottle 150, through the handpiece 114 to the irrigation port 102.

The effectiveness of a surgical instrument for phacoemulsification depends on the rate at which tissue is removed, which may be substantially affected by cavitation since cavitation may reduce partial or total occlusions of the hollow titanium needle 106. On the other hand, a particle engaged with the hollow titanium needle 106 by vacuum may partially disintegrate if the ultrasonic energy causes high cavitation. In this case, the surgeon may lose the particle and additional maneuvers may be necessary to reengage. Retention of tissue particles in engagement with the hollow titanium needle 106 is desirable and may be referred to as "followability." To improve followability, reduced cavitation during phacoemulsification may be advantageous.

One way to reduce cavitation is to excite the hollow titanium needle 106 to vibrate torsionally rather than longitudinally, so that the needle tip alternately rotates clockwise and counter-clockwise in relation to its longitudinal axis. Torsional vibrations do not readily propagate as waves in fluid, so that cavitation effects are substantially reduced. However a needle tip 108 that is vibrating purely torsionally may too easily core into the lens material without sufficient disintegration of tissue into particles, which, in turn, may too frequently lead to total occlusions in the hollow titanium needle 106.

According to one of the embodiments of the present invention disclosed herein, followability may be enhanced by longitudinally ringing a hollow titanium needle 106 at a carefully selected and substantially higher frequency than has been used previously for phacoemulsification. Most preferably, the ringing frequency is chosen so that the phacoemulsification needle length corresponds to approximately three quarter vibration wavelengths. Such a higher ultrasonic frequency, in combination with the proper length of the hollow titanium needle 106, may lead to reduced heating of tissue at the incision in the cornea, this is considered a "cold" needle, and may generate larger numbers but smaller sized cavitation bubbles per unit volume. The energy delivered by a cavitation bubble is related to the bubble radius, which in turn is inversely related to the frequency of vibration. For example, a bubble size generated by a 40 kHz wave may be approximately 41 μm, while being only 7.6 μm at 215 kHz. When more and smaller bubbles are generated, cavitation patterns may be more uniformly distributed over the cutting area, which, in turn, may enhance followability relative to phacoemulsification needle's operating with conventional longitudinal ultrasonic vibrations.

Figure 3:
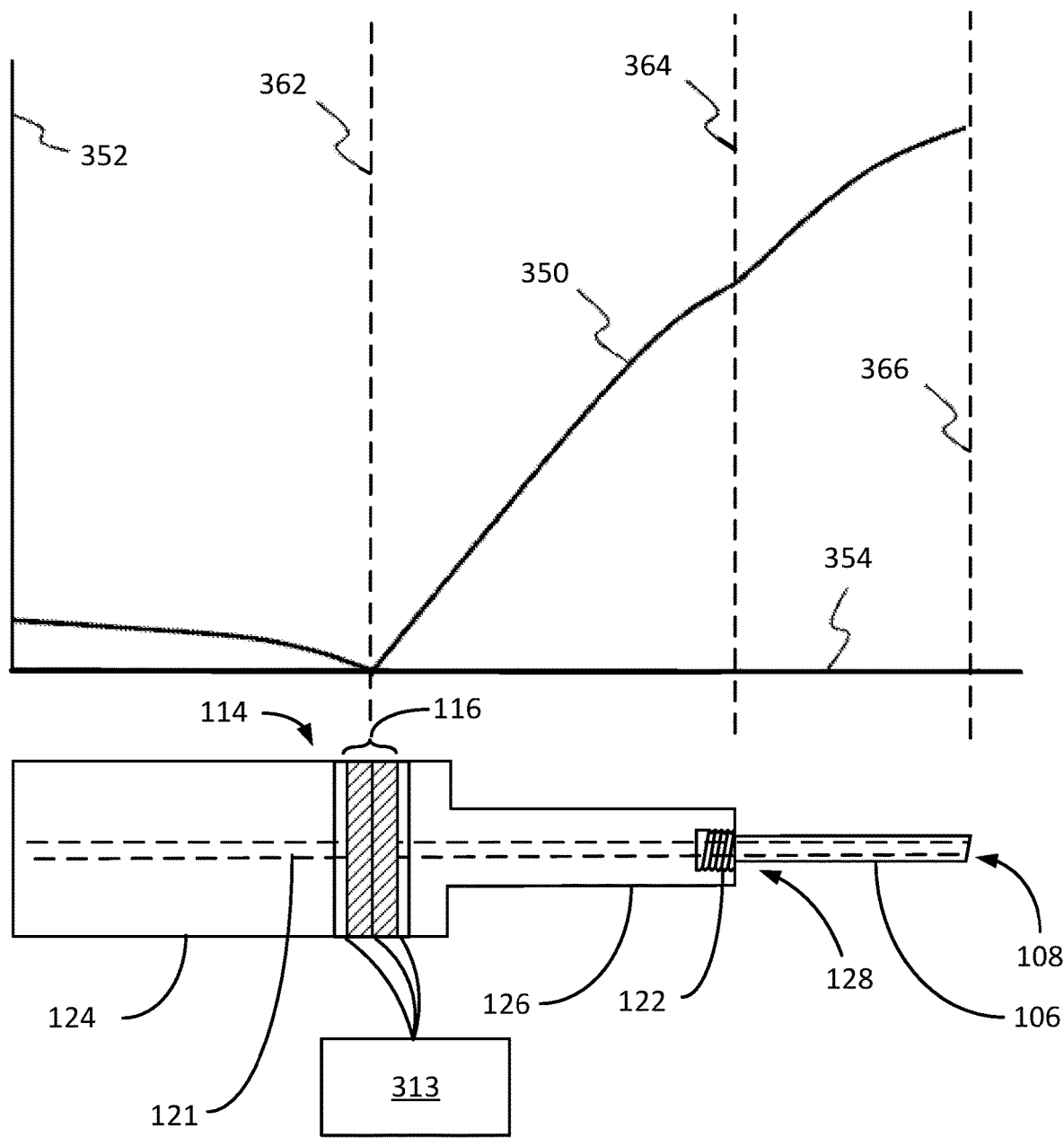
FIG. 3 illustratively depicts a line drawing of an embodiment of a handpiece and hollow titanium needle operating at an ultrasonic frequency against a graphical plot of the ultrasonic frequency response consistent with embodiments of the present invention.

FIG. 3 depicts an embodiment of a handpiece 114 for longitudinal vibration of the hollow titanium phacoemulsification needle 106, operating at an ultrasonic frequency between 20 kHz and 100 kHz. The handpiece 114 includes a back cylinder 124 and a front cylinder 126 compressing a pair of piezoelectric crystals 115, 117 sandwiched via a central bolt (not shown). Some embodiments contemplate four or six piezoelectric crystals or more. The piezoelectric crystals 115, 117 are driven by a circuit 313 that provides an oscillating voltage to the piezoelectric transducer 116/124. The wavelength λ of a longitudinally ringing structure is given by the formula λ=c/f where c is the speed of sound through the structure's material and f is the frequency of operation. Titanium material exhibits a speed of sound that is approximately 4,876,800 mm/sec. Accordingly, the hollow titanium needle 106 longitudinally vibrating at a frequency of 40 kHz (40000 Hz) has a wavelength of (4,876,800 mm/s)/(40,000 Hz)=122 mm.

In FIG. 3, the combined length of the front and back cylinders 126, 124 is approximately ½ wavelength during conventional ultrasonic operation, with a node of zero vibration amplitude at a location 362 at the interface between the two piezoelectric crystals 115, 117. For that reason, the handpiece 114 may be referred to as a "half-wavelength horn."

Figure 3A:
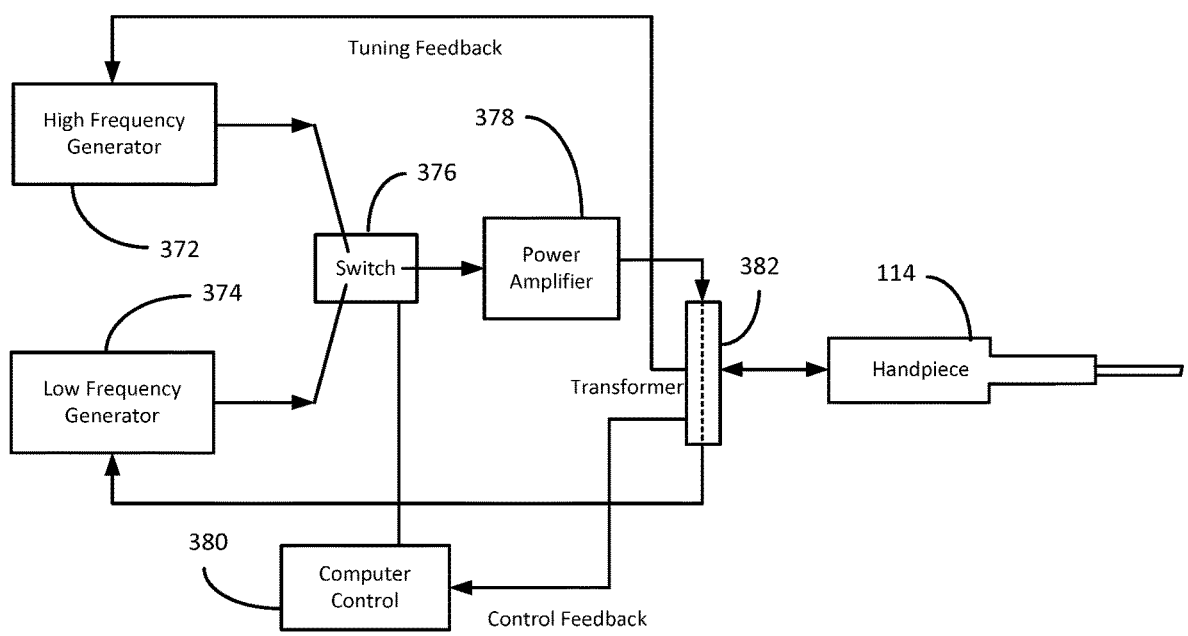
FIG. 3A is a block diagram illustratively depicting an embodiment of a control feedback circuit consistent with embodiments of the present invention.

FIG. 3A is a block diagram illustratively depicting an embodiment of a control feedback circuit 313 that provides an oscillating voltage to the piezoelectric transducer 116/124. Generally shown is a high frequency generator 372 that provides high ultrasonic frequency voltage input to the piezoelectric transducer 116/124 in the handpiece 114 and a lower frequency generator 374 that provides ultrasonic frequency voltage input to the piezoelectric transducer 116/124 in the handpiece 114 via the switch 376, power amplifier 378 and a transformer 382. More specifically, a computer control unit 380 sends signals to modulate input from either the high frequency generator 372 or the low frequency generator 374, wherein that signal (from one of the generators 372, 374) passes through the switch 376 where it is amplified by the power amplifier 376 and then translated to the two piezoelectric crystals 115, 117 via the transformer 382 to drive the hollow titanium needle 106 with the desired frequency wave. This control feedback circuit 313 is arranged to detect slight impedance changes of the transducer 116/124, thus being capable to sensing increased loading to the system, e.g., an engaged particle occluding the hollow titanium needle 106, causing the computer controller 380 to toggle the switch 376 (or vice versa if the particle is no longer engaged with the hollow titanium needle 106).

FIG. 3 is not drawn to scale, so that the hollow titanium phacoemulsification needle 106 may be more clearly depicted as a hollow cylinder. The hollow titanium needle 106 can be attached to the handpiece 114 using threads 122. One embodiment contemplates the length of the hollow titanium needle 106 having a small cross-sectional area with a length that is less than ¼ wavelength (30.5 mm at 40 kHz), for example 17 mm. The mass of the hollow titanium needle 106 is also small when compared with the mass of the handpiece 114. Consequently, the hollow titanium needle 106 does not dramatically change the dynamic resonance characteristics of the handpiece 114. As discussed previously, the hollow titanium needle 106 includes a narrow tubular passage 121 there through. The tubular passage 121 continues through the entire handpiece 114 so that fluid and tissue can be aspirated through the hollow titanium needle 106 to an aspiration tube that is connected to the handpiece 114. The aspiration tube is linked to a pump 154 that provides sub-ambient pressure to the narrow tubular passage 121 to suck aspirated material from the eye 120.

The cross sectional area of the front cylinder 126 of the handpiece 114 is smaller than the cross section area of the back cylinder 124, in order to provide displacement magnification as shown in the graph 350 in the upper portion of FIG. 3. Specifically the displacement at the rightmost extent 364 of the front cylinder 126 may be about 20 times the displacement at the leftmost edge 352 of the rear cylinder 124. Note that the vertical axis 352 of the graph 350 represents displacement amplitude (longitudinal compression and expansion increasing upwards). The horizontal axis 354 of the graph 350 represents the longitudinal coordinate along the length of the handpiece 114 and hollow titanium needle 106. Longitudinal strain in the hollow titanium needle 106 marginally increases displacement plotted in graph 350, though the entire hollow titanium needle 106 longitudinally translates. For example, the displacement at the location 366 of the distal end 108 of the hollow titanium needle 118 is somewhat greater than the displacement at the rightmost extent 364 of the front cylinder 126. Note that there is no location of zero vibration (i.e. nodal point) along the length of the hollow titanium needle 106.

One embodiment contemplates the hollow titanium needle 106 being substantially cylindrical, with an outer diameter in the range 0.5 mm to 1.5 mm and a length in the range 12 mm to 37 mm, the length being defined along a longitudinal axis of the hollow titanium needle 106 (i.e. parallel to graph axis 354). In this context "cylindrical" does not necessarily mean cylindrical with a circular or annular cross section. Rather, any closed hollow extruded shape may be used (e.g. a closed hollow square cross-section). However, an annular cross-section having circular inner and outer peripheries may be preferred for manufacturability.

Figure 4:
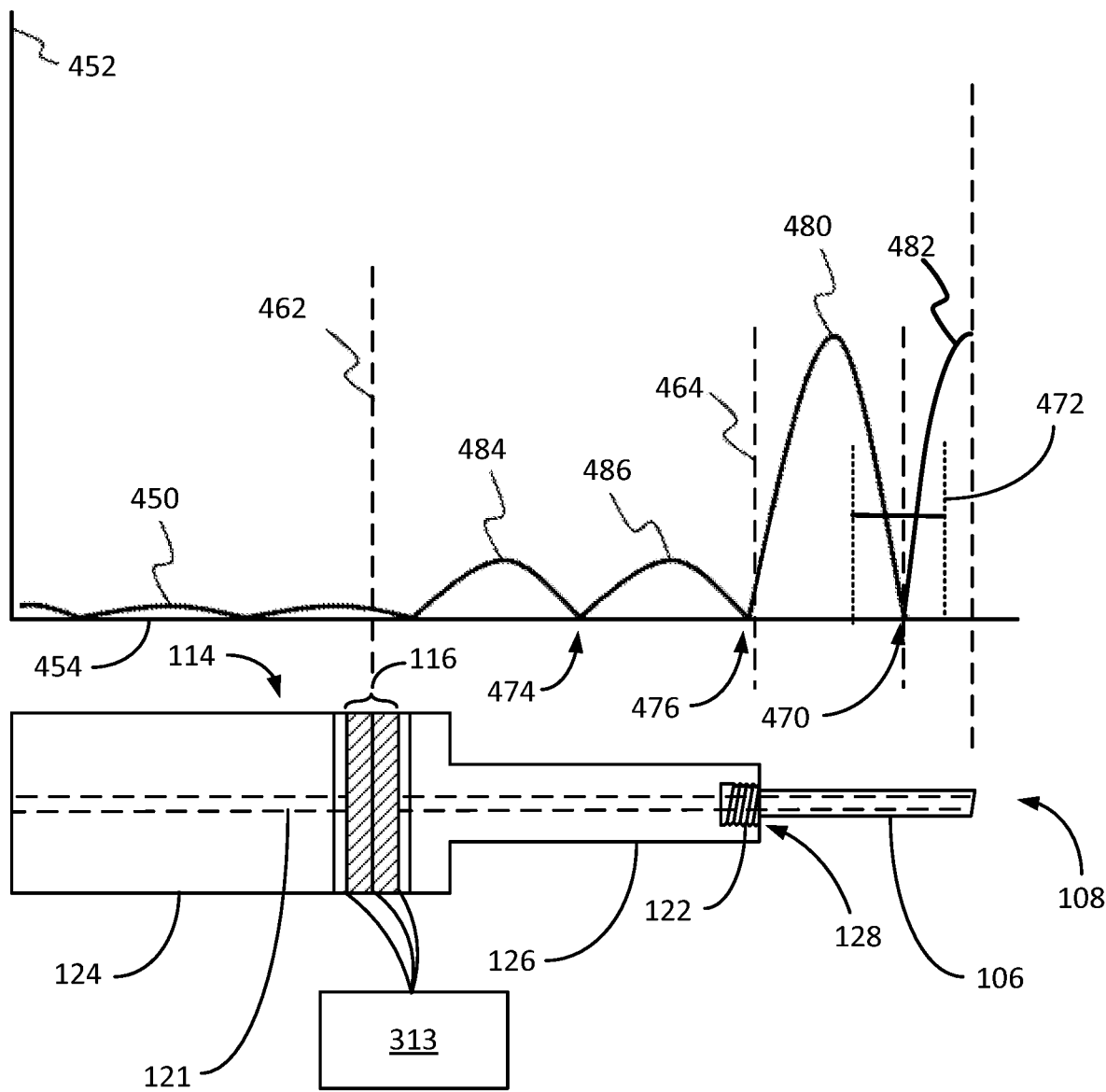
FIG. 4 illustratively depicts a line drawing of an embodiment of a handpiece and hollow titanium needle operating at a high ultrasonic frequency against a graphical plot of the high ultrasonic frequency response consistent with embodiments of the present invention.

FIG. 4 depicts an embodiment of the surgical instrument of FIG. 3 whereby the handpiece 114 is ringing the hollow titanium needle 106 at a high ultrasonic frequency, above 60 kHz. As previously described, the handpiece 114 includes a piezoelectric transducer 116/124, wherein the transducer 116/124 comprises a sandwich structure of two piezoelectric elements 115, 117, which meet at an interface location 462 in-between the back cylinder 124A and 124B. The piezoelectric elements 115, 117 may comprise piezoelectric ceramics or crystals, preloaded to be in compression by a bolt in tension, for example.

The front cylinder 126 may also be generally comprised by titanium, for example, to match the speed of sound of the hollow titanium needle 106 and thereby reduce acoustic reflections at the interface between the front cylinder 126 and the titanium needle 106.

The surgical instrument depicted in FIG. 4 includes a circuit 313 that provides an oscillating voltage to the piezoelectric transducer 116/124 in the handpiece 114, the voltage oscillating at a driving frequency that rings the hollow titanium needle 106 at different ultrasonic frequencies with corresponding standing waves characterized by longitudinal expansion and longitudinal contraction. In certain embodiments, the frequency with which the circuit 313 drives the piezoelectric transducer 116 is preferably in a range below 100 KHz, or several ranges, such as above 60 KHz and below 60 KHz. For example, in this embodiment, the total length of the hollow titanium needle 106 may be approximately 17 mm, and the driving frequency may be above 60 KHz. Higher frequencies may introduce additional nodal waves along the length of the titanium needle 106.

Such dimensional ranges and driving frequencies may advantageously result in three quarter wavelengths of the longitudinal standing wave lying along the hollow titanium needle 106 if it is a titanium needle of 17 mm total length. This can be verified by referring again to the formula $\lambda=c/f$. Specifically, according to this formula the wavelength of the standing longitudinal wave in a titanium needle in this configuration would be (4,876,800 mm/s)/215,000 Hz)=22.7 mm. Hence, approximately three quarter wavelengths would lie along a needle length of 17 mm.

An example of the amplitude of the longitudinal expansion and longitudinal contraction causing displacement along the handpiece 114 and the hollow titanium needle 106, according to an embodiment of the present invention, is plotted versus longitudinal position in the graph 450 that appears above the handpiece 114 in FIG. 4. The vertical axis 452 of the graph 450 represents displacement amplitude (increasing upwards). The graph 450 illustratively depicts dimensionless values of the displacement amplitude. The horizontal axis 454 of the graph 450 represents the longitudinal coordinate along the length of the handpiece 114 and the hollow titanium needle 106.

In the embodiment of FIG. 4, the standing wave shown in graph 450 preferably has a distal node of minimum amplitude at a node location 470 on the substantially cylindrical hollow titanium needle 106. That is depicted on the graph 450 as a minimum point at the node location 470. Unlike ultrasonic vibrations in a range under 100 kHz (e.g. like that shown in FIG. 3), the portion of the hollow titanium needle 106 that is most likely to contact the incision in the cornea, may be in a region 472 that includes a minimum node in the standing wave of vibration, and therefore experiences a much lower motion than does the distal tip 108. In certain embodiments, this may advantageously reduce heating of the tissue at and near the incision in the cornea.

Figure 5:
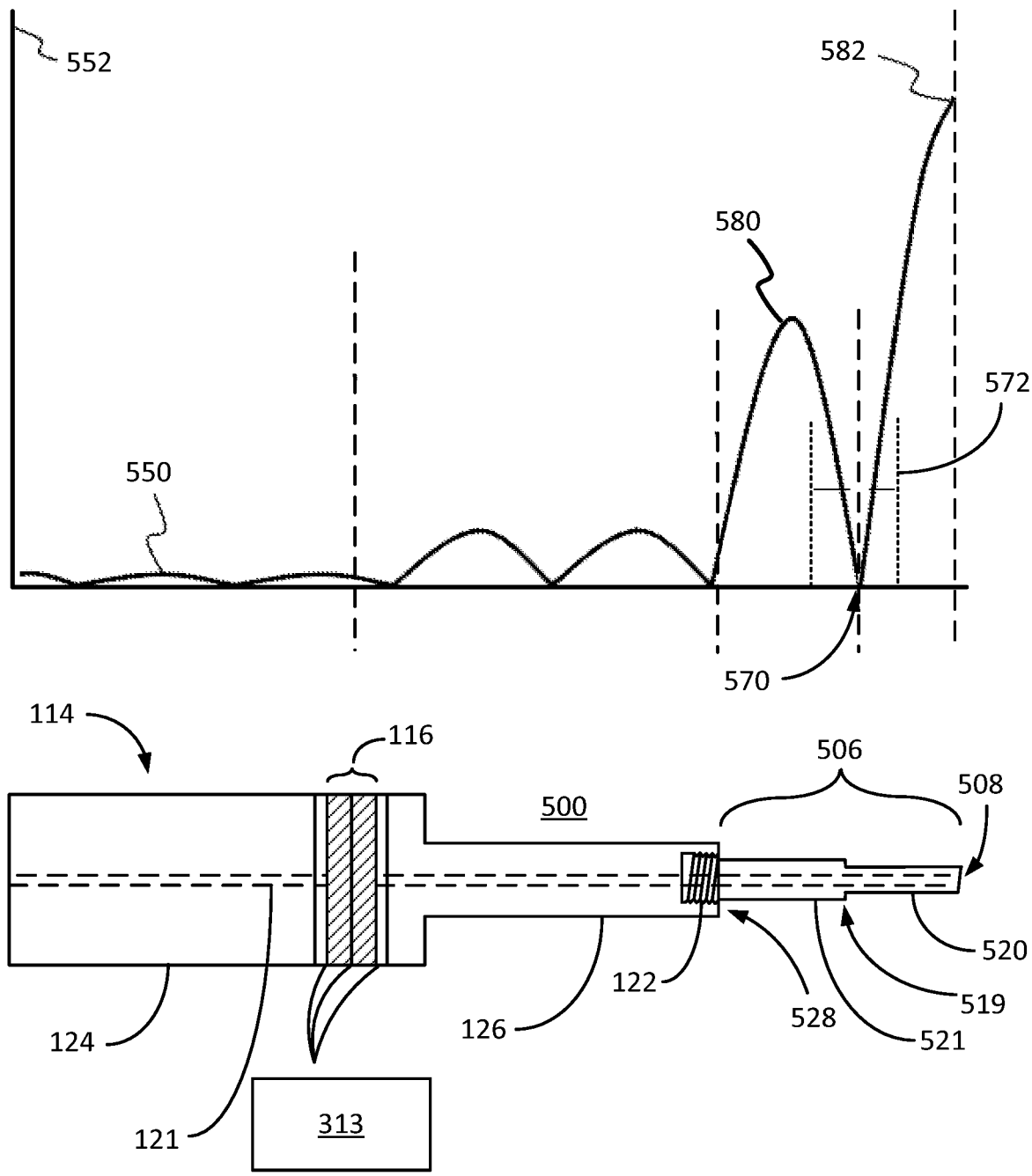
FIG. 5 illustratively depicts a line drawing of an embodiment of a handpiece and hollow titanium needle with a shoulder in the substantially cylindrical portion of the needle consistent with embodiments of the present invention.

One optional embodiment depicted in FIG. 5 contemplates the hollow titanium needle 506 to include a shoulder 519 where the outer diameter of hollow titanium needle 506 changes. The hollow titanium needle 506 includes a first substantially cylindrical portion 520 between the shoulder 519 and the free distal tip 508, and a second substantially cylindrical portion 521 between the shoulder 519 and the supported end 528. In this case, the shoulder 519 is preferably disposed between 5 mm to 8 mm from the free distal tip 508. The outer diameter of the hollow titanium needle 506 is preferably less in the first substantially cylindrical portion 520 than in the second substantially cylindrical portion 521; as such inequality may advantageously amplify the ringing amplitude in the first substantially cylindrical portion 520 as illustratively depicted by the graph 550 when the hollow titanium needle 506 is subjected to a high ultrasonic frequency. In more detail, there is a distal node of minimum amplitude at a node location 570 on the substantially cylindrical hollow titanium needle 506. Also, in the embodiment of FIG. 5, the standing wave shown in graph 550 may have a distal anti-node 582 of maximum amplitude at the free distal tip 108 (which has a peak higher than the amplitude of the anti-node 580 because the hollow titanium needle 109 possesses the thinner first substantially cylindrical portion 520 in this embodiment), so that high displacement amplitude at the distal tip 108 can enhance tissue penetration by the distal tip 108.

In certain embodiments, including certain embodiments that lack any shoulder 519, the reduced corneal incision heating advantage may be obtained by the distal node of minimum amplitude (at node location 470) being preferably disposed between 5 mm to 8 mm from the free distal tip 108. Although in the embodiment of FIG. 5 the shoulder 519 is depicted as being immediately adjacent the distal node of minimum amplitude (at node location 470), there is no requirement for that, and indeed in certain embodiments it is preferred that they not be at the same longitudinal location. For example, in certain embodiments, it is preferred that the distal node of minimum amplitude (at node location 470) be disposed more distally (to the right in FIG. 5) than the shoulder 519.

In the embodiment of FIG. 4, the standing wave shown in graph 450 has a proximal node of minimum amplitude 476 near or adjacent the supported end 128. That is depicted as a minimum point on the graph 450, just to the left of the location 464. Note that the proximal node of minimum amplitude 476 is not the same as the distal node at node location 470, and it does not serve the same purposes as described for the distal node at node location 470. Also, in the embodiment of FIG. 4, the standing wave shown in graph 450 may have a distal anti-node 482 of maximum amplitude at the free distal tip 108 (which has a peak at essentially the same amplitude as the anti-node 480 because the hollow titanium needle 109 is a constant thickness in this embodiment), so that high displacement amplitude at the distal tip 108 can enhance tissue penetration by the distal tip 108.

Other nodes (e.g. node 474) may exist in the displacement amplitude graph along the front cylinder 126, but these are not the same as the distal node at node location 470, nor do they serve the same purposes as described for the distal node at node location 470. Another anti-node 480 may exist in the substantially cylindrical portion of the hollow titanium needle 106, but it does not serve the same purpose as does the distal anti-node 482 of maximum amplitude at the free distal tip 108. However, in certain embodiments, the existence and location of the anti-node 480 is an expected consequence of the desired placement of the distal node of minimum amplitude at a node location 470 on the substantially cylindrical hollow titanium needle 106 (as described in previous paragraphs). Other anti-nodes (e.g. anti-nodes 484, 486) may exist in the displacement amplitude graph along the front cylinder 126, but these are not the same as the distal anti-node 482 of maximum amplitude at the free distal tip 108, nor do they serve the same purpose as does the distal anti-node 482 of maximum amplitude at the free distal tip 108

Embodiments of the present invention contemplate switching vibrations to the hollow titanium needle 106 between ultrasonic frequency and high ultrasonic frequency. As previously discussed, at high ultrasonic frequency (FIG. 4) there is a node of minimum amplitude 470 along the substantially cylindrical portion of the hollow titanium needle 106 between the distal free end 108 and the supported end 128 whereby near or at the distal node of minimum amplitude 470 there is little to no heat generated. This is considered to be a "cold" needle. The circuit 313 is adapted to modulate, or change, the frequency between the ultrasonic frequency and high ultrasonic frequency.

Certain embodiments contemplate a routine (either in hardware or in software) that causes the circuit 313 to modulate frequencies driving the hollow titanium needle 106 between the ultrasonic frequency and high ultrasonic frequency after a predetermined time interval. One embodiment envisions the frequency modulating between ultrasonic frequency and high ultrasonic frequency in a symmetrical amount of time. For example, after every 5 seconds (or some other amount of time) the circuit 313 drives the hollow titanium needle 106 from the ultrasonic frequency to the high ultrasonic frequency and then back again. Yet another example includes causing the circuit 313 to change from ultrasonic to high ultrasonic in an asymmetric amount of time, such as for example, 5 seconds (or some other amount of time) at ultrasonic frequency then 3 seconds (or some other amount of time) at high ultrasonic frequency and then repeat. The predetermined amount of time is envisioned to be set either manually by someone in the operating room or default routines set by the manufacturer, just to name a couple of examples to set a predetermined amount of time. Other certain embodiments contemplate manual intervention to modulate frequencies driving the hollow titanium needle 106 between the ultrasonic frequency and high ultrasonic frequency. One embodiment envisions a foot pedal or other manually operated switching device (or potentiometer) modulating the frequency between ultrasonic frequency and high ultrasonic frequency. The software that controls the different frequencies can be executed via the computer controller 380 or equivalent computing device.

Figure 6:
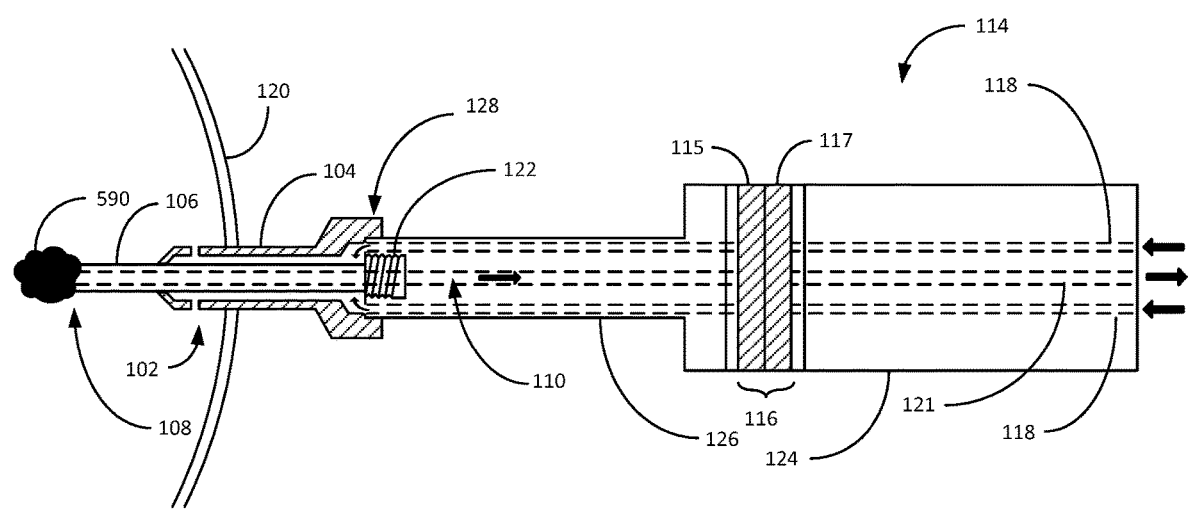
FIG. 6 illustratively depicts a line drawing of an occluding particle obstructing the aspiration pathway at the free distal tip of a hollow titanium needle consistent with embodiments of the present invention.

Yet other certain embodiments contemplate an event during a phacoemulsification procedure that drives the hollow titanium needle 106 to modulate from between the ultrasonic frequency and high ultrasonic frequency. For example, and with reference to FIG. 6, depicted is a particle 590, such as lens material, that is occluding the aspiration pathway 121 at the free distal tip 108 of the hollow titanium needle 106. When a particle 590 is engaged in such a way, it can decrease flow rate in an aspiration pathway 121. For example, with a peristaltic pump, the aspiration flow rate is always constant. The pump automatically increases vacuum to overcome an increased resistance to flow. If an occlusion (such as from the particle 590) is not cleared by the maximum vacuum the pump can create, the flow drops to zero. Hence, the flow rate is either constant or zero. With a Venturi type pump, the flow rate decreases or increases as a function of pipe resistance, which can be caused by an occlusion (such as from the particle 590). In either situation, the irrigation flow along pathway 118 is reduced or drops to zero to match the pump flow rate in order to maintain proper IOP. A reduction or stoppage of irrigation fluid can cause localized heating at the cornea. In this situation, increasing the frequency of the hollow titanium needle from ultrasonic to high ultrasonic can reduce localized heating at the incision site of the cornea and can help break up the particle 590 to allow aspiration and irrigation to proceed normally at an unblocked flow rate.

Feedback in the phacoemulsification system 148 to an occlusion or partial occlusion of the aspiration pathway 121 due to a particle 590 can be used to trigger the hollow titanium needle 106 to modulate from the ultrasonic frequency and the high ultrasonic frequency (or optionally back and forth) to break up the particle 590 and reduce heating at the corneal incision during a phacoemulsification procedure. Some embodiments contemplate using feedback in the phacoemulsification system 148 to identify a particle engaged in an occluding or partial occluding manner includes a diminishing change in aspiration flow rate of ocular material aspirated from an eye 120, a diminishing change in irrigation flow rate of irrigation fluid into the eye 120, an increasing change in aspiration vacuum or how much harder an aspiration pump 154 has to work to aspirate ocular material from the eye 120 increases, or an increase in load to drive the frequency of the hollow titanium needle 106 due to an increased mass of a particle engaged/lodged in or on the hollow titanium needle 106.

Some embodiments contemplate identifying the presence of a particle 590 either occluding or partially occluding the aspiration path 121 based on a diminishing change in aspiration flow rate of the aspirated ocular material from the eye 120. A sensor (not shown) can be located in the infusion/irrigation pathway 118, or elsewhere, to sense a diminished flow rate of aspirated ocular material from the eye 120. Shifting ringing the hollow titanium needle 106 from an ultrasonic frequency to a high ultrasonic frequency can help break apart an occluding particle 590 and reduce heating at the cornea incision (or optionally ringing back and forth between the two frequencies). When the aspiration ocular material is flowing at an expected flow rate that does not reflect an occluded or partially occluded aspiration pathway 121, the circuit 313 can drive the hollow titanium needle 106 to ring back at the ultrasonic frequency.

Some embodiments contemplate identifying the presence of a particle 590 either occluding or partially occluding the aspiration path 121 based on a diminishing change in irrigation flow rate of irrigation fluid into the eye 120. A sensor (not shown) can be located in the infusion/irrigation pathway 118, or elsewhere, to sense a diminished flow rate of irrigation fluid into the eye 120. Shifting ringing the hollow titanium needle 106 from an ultrasonic frequency to a high ultrasonic frequency can help break apart an occluding particle 590 and reduce heating at the cornea incision (or optionally ringing back and forth between the two frequencies). When the infusion/irrigation pathway 118 is flowing irrigation fluid at an expected flow rate that does not reflect an occluded or partially occluded aspiration pathway 121, the circuit 313 can drive the hollow titanium needle 106 to ring back at the ultrasonic frequency.

Some embodiments contemplate identifying the presence of a particle 590 either occluding or partially occluding the aspiration path 121 based on an increase in vacuum pressure (negative pressure) generated by the aspiration pump 154 (such as by back electro-magnetic force (EMF) of the pump or an inline sensor, for example) above what is considered a normal resistance to flow. Shifting ringing the hollow titanium needle 106 from an ultrasonic frequency to a high ultrasonic frequency can help break apart an occluding particle 590 and reduce heating at the cornea incision (or optionally ringing back and forth between the two frequencies). When the aspiration pump 154 is functioning at an expected vacuum level that does not reflect an occluded or partially occluded aspiration pathway 121, the circuit 313 can drive the hollow titanium needle 106 to ring back at the ultrasonic frequency.

Some embodiments contemplate identifying the presence of a particle 590 either occluding or partially occluding the aspiration path 121 based on an increase in mass of the hollow titanium needle 106 due to a particle engaged therewith in an occluding/partially occluding manner. The transducer 116/124, for example, can be used to sense an increase in mass of the hollow titanium needle 106 due to an engaged particle based on an increase in voltage load to drive the frequency via the transducer 116/124. Shifting ringing the hollow titanium needle 106 from an ultrasonic frequency to a high ultrasonic frequency can help break apart an occluding particle 590 and reduce heating at the cornea incision (or optionally ringing back and forth between the two frequencies). When the mass of the hollow titanium needle 106 returns to a level that does not reflect an increased mass of the hollow titanium needle 106, the circuit 313 can drive the hollow titanium needle 106 to ring back at the ultrasonic frequency.

Certain embodiments of the present invention contemplate employing frequencies ringing the hollow titanium needle 106 in a manner vice versa to the above embodiments describing ultrasonic frequencies modulating to high ultrasonic frequencies. For example, generally ringing the hollow titanium needle 106 at a high ultrasonic frequency and then modulating the ringing to an ultrasonic frequency may improve breaking up an occluding particle 590. For example, an occlusion may be cleared faster at ultrasonic frequencies where cavitation effects are stronger and whereby larger bubbles are generated by lower ultrasonic frequency waves. In one illustrative example, the hollow titanium needle 106 can be made to ring at a high ultrasonic frequency but then be made to ring at an ultrasonic frequency when the hollow titanium needle 106 becomes occluded. Once the hollow titanium needle 106 is no longer occluded, the hollow titanium needle 106 is then made to ring at the high ultrasonic frequency.

Embodiments of the present invention contemplate ringing the hollow titanium needle 106 between the ultrasonic frequency range (20 kHz-100 kHz) and a sonic frequency range (less than 20 kHz). A sonic frequency, or frequency that is in the sound range, greatly reduces the heating effects of vibration on the hollow titanium needle 106. A sonically vibrating hollow titanium needle 106 is considered a "cold" needle because there is little risk of burning the incision site of the cornea. Much like the embodiments described herein that are directed to modulating the frequency ringing the hollow titanium needle 106 between an ultrasonic frequency and a high ultrasonic frequency, the same embodiments are further contemplated using the condition where sonic frequency is substituted in place of the high ultrasonic frequency. In other words, embodiments herein are further envisioned to modulate the hollow titanium needle 106 from ultrasonic frequency to sonic frequency when there is an occlusion or partial occlusion, or optionally when a surgeon wants to manually switch between ultrasonic and sonic frequencies, or optionally toggling between the two after a predetermined amount of time, for example.

Certain embodiments of the present invention contemplate employing frequencies ringing the hollow titanium needle 106 in a manner vice versa to the above embodiments describing ultrasonic frequencies modulating to sonic frequencies. For example, generally ringing the hollow titanium needle 106 at a sonic frequency and then modulating to an ultrasonic frequency to break up an occluding particle 590.

Figure 7A:
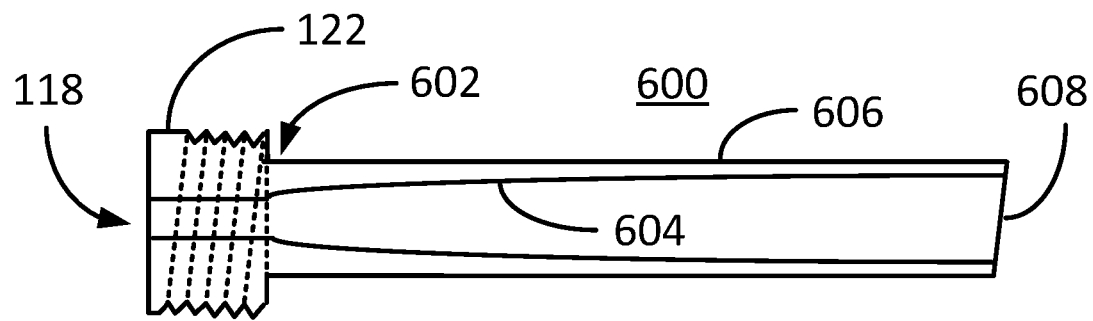
FIG. 7A-7D illustratively depict a line drawing of optional bore profiles in a hollow titanium needle consistent with embodiments of the present invention.
Figure 7B:
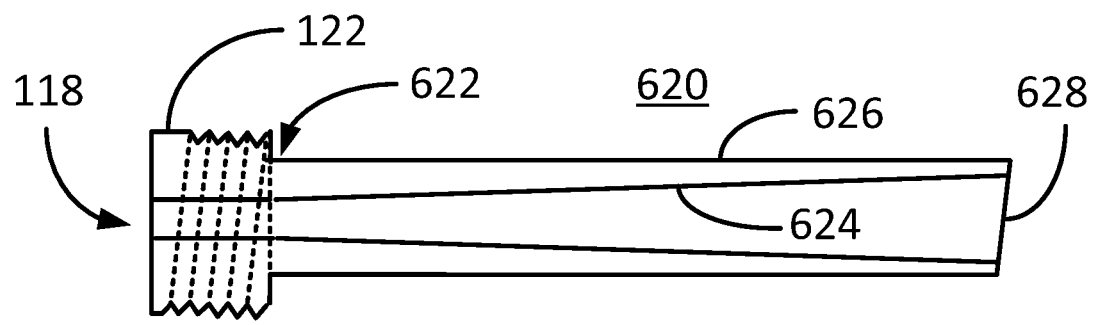
Figure 7C:
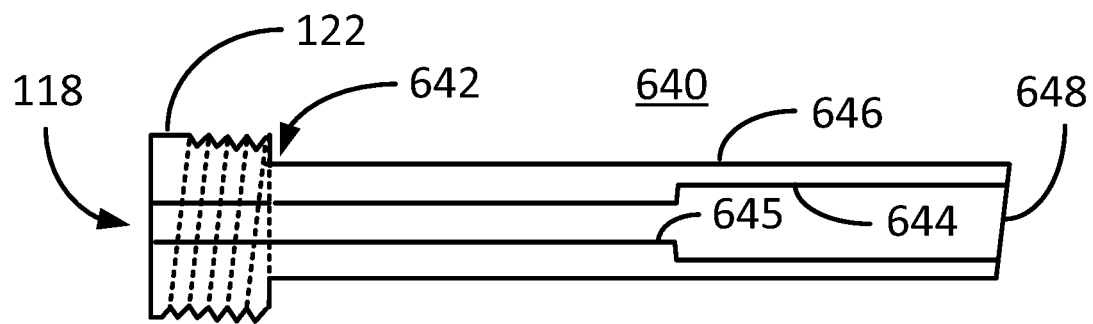
Figure 7D:
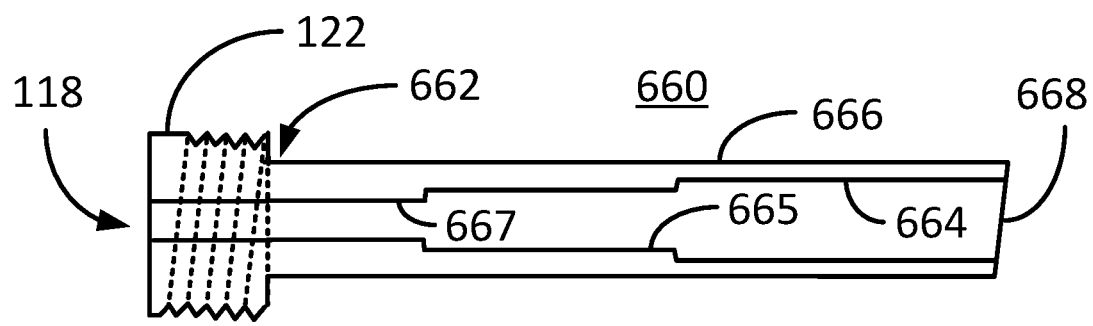

FIGS. 7A-7D contemplate alternate inner bore geometries wherein embodiments of the present invention can be practiced. FIG. 7A illustratively depicts a hollow titanium needle 600 comprising an elliptical shaped bore 604 that possesses a thicker needle wall as it approaches the supported end 602 and a thinner needle wall as it approaches the free distal tip 608. The outer needle diameter 606 is essentially consistent between the supported end structure 122 and the free distal tip 608. FIG. 7B illustratively depicts another embodiment of a hollow titanium needle 620 comprising an linear angulated bore 624 that possesses a thicker needle wall as it approaches the supported end 622 and a thinner needle wall as it approaches the free distal tip 628. The outer needle diameter 626 is essentially consistent between the supported end structure 122 and the free distal tip 628. FIG. 7C illustratively depicts yet another embodiment of a hollow titanium needle 640 comprising an internal stepped bore 644, 645 that possesses a thicker needle wall 645 proximal to the supported end 642 that steps to a thinner needle wall 644 as it approaches the free distal tip 648. The outer needle diameter 646 is essentially consistent between the supported end structure 122 and the free distal tip 648. FIG. 7D illustratively depicts yet another embodiment of a hollow titanium needle 660 comprising an internal stepped bore 664, 665, and 667 that possesses a thickest needle wall 667 proximal to the supported end 662 that steps to an intermediate thickness wall 665, than steps to a thinner needle wall 664 as it approaches the free distal tip 668. The outer needle diameter 666 is essentially consistent between the supported end structure 122 and the free distal tip 668. Though the step 645 in FIG. 7C and the steps 665 and 667 in FIG. 7D have thicknesses that are essentially parallel to the outer diameter of the hollow titanium needle 646 and 666, certain embodiments contemplate such a condition not required, wherein the thicknesses can be tapered, curved, etc., within the scope and spirit of different thickness bores. Moreover, the different thickness bores may be implemented to alter the frequency profile to create nodes of minimum amplitude or create varied frequency responses at specific locations along the length of the hollow titanium needle.

Figure 8:
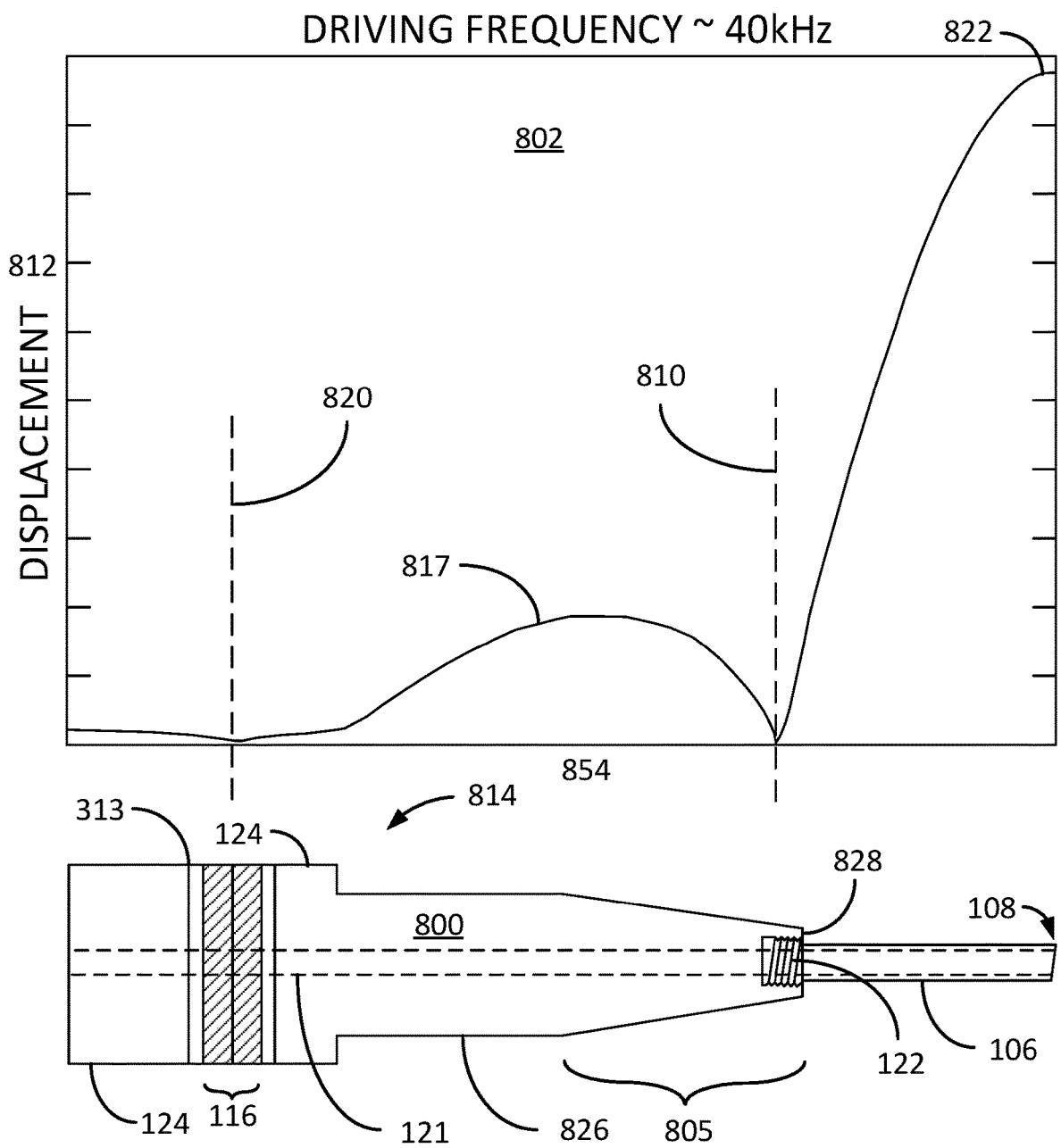
FIG. 8 illustratively depicts a line drawing of an optional embodiment of a handpiece with respect to a driving frequency of approximately 40 kHz consistent with embodiments of the present invention.
Figure 9:
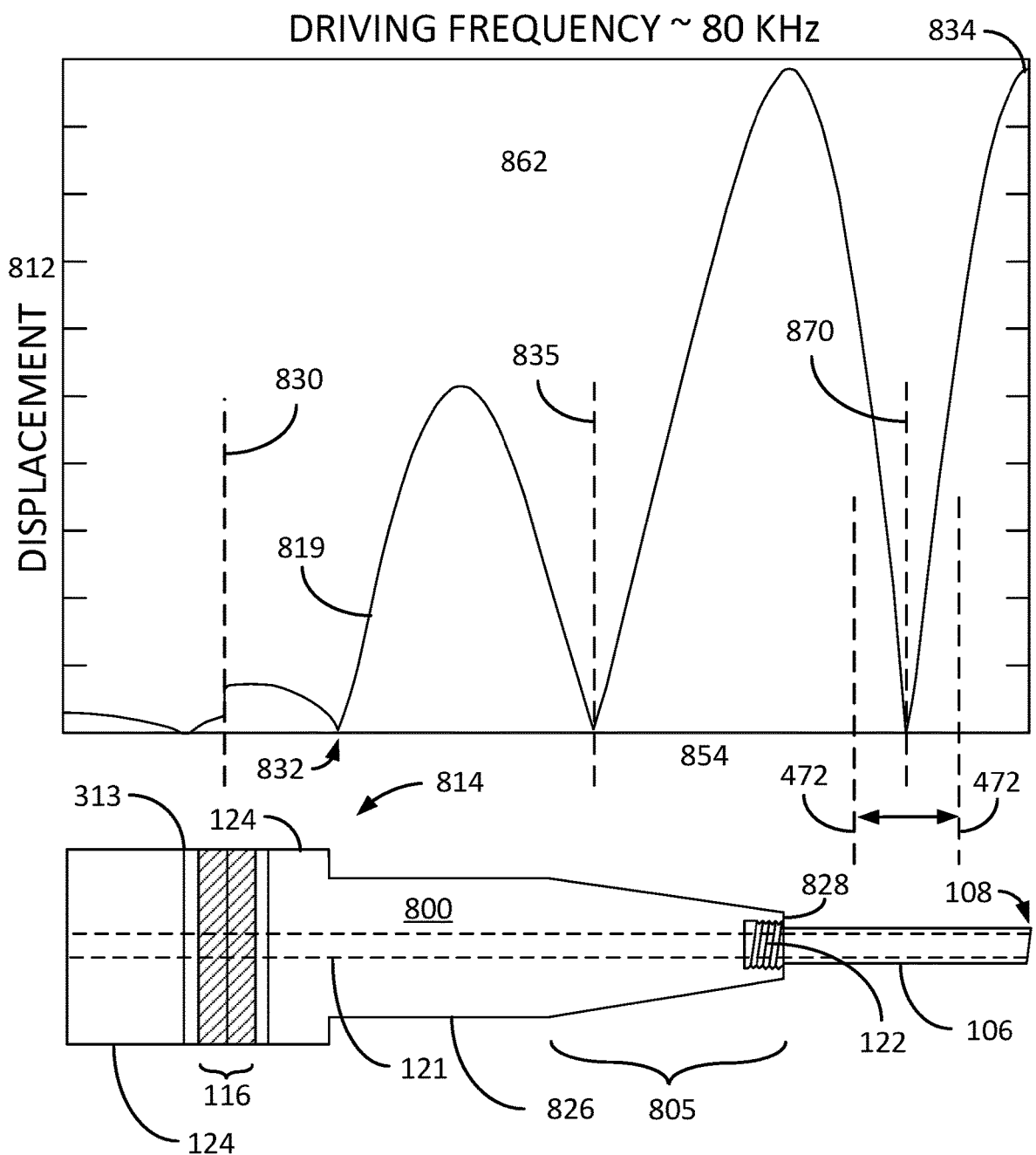
FIG. 9 illustratively depicts a line drawing of the handpiece of FIG. 8 with respect to a driving frequency of approximately 80 kHz consistent with embodiments of the present invention.

FIG. 8 illustratively depicts an optional embodiment of a handpiece with respect to a driving frequency of approximately 40 kHz consistent with embodiments of the present invention. An example of a driving frequency is an applied resonant frequency that excites the element that is subjected to the driving frequency to resonate with a standing wave as shown in FIGS. 8 and 9. The phacoemulsification device embodiment 800, the handpiece 814 includes a back cylinder 124 that comprises piezoelectric crystals that are driven by a circuit 313, which provides an oscillating voltage to the piezoelectric transducer 116/124. A typical back cylinder 124 (which as depicted in FIG. 1 includes a rear portion 124A and a front portion 124B) construction includes two or more piezo ceramic discs 116 sandwiched between two metal cylinders usually made of titanium and compressed through a central bolt. Certain embodiments envision a Langevin transducer made up of four PZT8 piezo ceramics sandwich between a stainless steel rod and a titanium rod. The two or more piezo ceramic discs 116 convert an applied voltage to longitudinal expansion and contraction otherwise known as "Langevin transducer". A step horn 826 is distal to the back cylinder 124 and the piezoelectric crystals 116. The step horn 826 comprises a tapered section 805 that tapers from a large diameter at the front cylinder 826 to a small diameter at the step horn distal end 828. Certain other embodiments envision the step horn 826 being a titanium cylinder with a smaller diameter than the Langevine transducer diameter. The aspiration pathway 121 extends through the handpiece 814 and the substantially cylindrical titanium needle (or just "needle") 106 exiting at a distal free end 108. The needle 106 may or may not be cylindrical because in some cases, the substantially cylindrical titanium needle 106 may be tapered approximately five-thousandths of an inch from the supported end 122 to the free distal tip 108, which is near cylindrical or substantially cylindrical. The needle 106 screws into the step horn distal end 828 via a supported end structure 122, which in this case are threads. A fastening hub (not shown) can further retained the needle 106 to the handpiece at the step horn distal end 828. Certain embodiments contemplate the needle length being 0.7 inches long and the hub length being about 0.15 inches long. Certain embodiments further contemplate the needle OD being between 0.042 and 0.032 inches with an ID being between 0.027 and 0.020 inches.

The length of the phacoemulsification device 800 spans the abscissa 854 with a vibration response graph/plot 802. The vibration response graph 802 plots the amplitude response 817 of the phacoemulsification device 800 at a driving frequency of approximately 40 kHz, defined by a low ultrasonic standing wave 817. A standing wave is the displacement of the element that is subject to a resonant frequency (or approximate resonant frequency that causes excited vibration of the element), such as the handpiece 814 and needle 106. More specifically, the ordinate 812 of the graph 802 represents the displacement of the phacoemulsification device 800 and the abscissa 854 is the position/ length along the phacoemulsification device 800. Hence, the amplitude response plot 817 is the vibrational displacement response 812 along the length of the phacoemulsification device 800. As shown by the amplitude response 817, at approximately 40 kHz is a handle node of minimum amplitude 820 between the two piezoelectric crystals 116 that form the transducer 116/124 and a tapered section node of minimum amplitude 810 in the tapered section 805. At this frequency, there is no node of minimum amplitude along the needle 106. Certain embodiments contemplate insuring no node of minimum amplitude by way of the tapered segment 805 being higher than ¼ of the low frequency wavelength, which in this case is around 40 kHz. For example, the length of the tapered section 805 must be at least 0.6 inches with a wavelength of 4.8 inches (traversing the device 800) at a resonant frequency of 40 kHz. A distal antinode 822 at the free distal tip 108 causes a high displacement that is effective in fragmenting and emulsifying a cataractous lens of a human eye 101. Certain embodiments envision a low driving frequency between 25 kHz and 45 kHz to provide both fragmentation and emulsification of cataractous lens material.

FIG. 9 illustratively depicts the handpiece of FIG. 8 with respect to a driving frequency of approximately 80 kHz consistent with embodiments of the present invention. As with FIG. 8, the length of the phacoemulsification device 800 spans the abscissa 854 with a vibration response graph/ plot 862. The vibration response graph 862 plots the amplitude response 819 of the phacoemulsification device 800 at a driving frequency of approximately 80 kHz, the amplitude response 819 defined by a high ultrasonic standing wave 819. More specifically, the ordinate 854 of the graph 862 corresponds with the position/length along the phacoemulsification device. Accordingly, the amplitude response plot 819 is the vibrational displacement response 812 along the length of the phacoemulsification device 800. As shown by the amplitude response 819 at 80 kHz there a number of different nodes of minimum amplitude including a) a handle node, b) a handle-step horn interface node 832, a tapered section node 835, and a needle node 870. There is a high amplitude, or high displacement, antinode 834 at approximately the free distal tip 108.

Some embodiments envision driving the frequency of the phacoemulsification device 800 between the low frequency of approximately 40 kHz and the high frequency of approximately 80 kHz to manage fragmentation and cavitation of cataractous lens material. Fragmentation is the action of cutting or splitting the lens in fragments like a knife moving very fast in a medium. In some cases, the fragments are sometimes too large to be sucked/aspirated through the aspiration pathway 121, let alone into the open tip 108. As discussed previously, this is a problem because a large fragment can occlude or otherwise block the aspiration pathway 121 at the free distal tip 108. Not only does a large fragment block the phacoemulsification device from operating, heat can build up along the needle 106 potentially burning the eye interface 101. At lower frequencies, under 60 kHz and more typically between 25 and 45 kHz, cavitation of the liquid in the eye 101 at the free distal tip 108 serves to emulsify or otherwise disintegrate the fragmented cataractous lens material into small particles that are small enough to pass through tip lumen (tip opening) and into the aspiration pathway 121. Intense cavitation induced waves may push the lens fragments away from the phaco tip 108, which complicates maneuvering the tip in the eye. These ways can also have negative effects by dislocating healthy eye tissue. There have been reports of fragmented cataractous lens material being pushed into the posterior portion of an eye 101. Higher frequencies, especially those over 60 kHz, generate less cavitation and above 100 kHz, cavitation almost disappears.

With this in mind, switching from a lower frequency under 60 kHz to a high frequency over 60 kHz has a number of benefits. For example, as shown in FIG. 9, at a high frequency the needle node of minimum amplitude 870 is considered a "cold needle" because there is no ultrasonic vibration occurring at the node of minimum amplitude 870. The needle node of minimum amplitude 870 is placed along the needle 106 depicted by the double arrow between the boundary lines 472. Hence, if the needle becomes occluded with a cataractous lens fragment at a low frequency, by switching to a high frequency the cataractous lens fragment can break up and be sucked through the aspiration pathway 121 more quickly and the needle 106 will not get overheated in the eye interface region 472. Furthermore, the high frequency reduces cavitation generation, which as previously mentioned has its own problems. Some embodiments contemplate the high frequency and the low frequency both being purely longitudinal waves.

The tapered region embodiment of the phacoemulsification device 800 can be lengthened, shortened, widened, etc., in order to better control the placement of a node of minimum amplitude along a needle 106 in a high frequency scenario. The geometry of the tapered region 805 further influences keeping a node of minimum amplitude from forming/existing along the needle 106. Certain other embodiments of the present invention do not limit the tapered region 805 from being conical but entertain additional shapes/profiles including elliptical, exponential, Gaussian, and Fourier, just to name a few. Certain commercial embodiments envision the total length of the handpiece 814 being approximately 3 inches long with a diameter of approximately 0.375 inches. The step horn 826 can be made of a titanium rod that is approximately 0.8 inches long and about 0.15 inches in diameter tapering conically down to 0.05 inches in diameter over a tapered region 805 that is approximately 1.2 inches long. The needle 106 can be approximately 0.8 inches long with an outside diameter of approximately 0.045 inches and an inside diameter of approximately 0.035 inches, which can open up to a handpiece pathway 121 that is about 0.07 inches in diameter. However, some embodiments envision a high frequency of above 60 kHz, which in some embodiments is approximately 80 kHz, and a low frequency below 60 kHz, which in some embodiments is approximately 40 kHz, other embodiments envision a low frequency below 50 kHz and the high frequency above 50 kHz. The phacoemulsification device 800 can be made to toggle between the low frequency and the high frequency automatically with the feedback system that takes into account vacuum, flow rate, bottle height, procedure modes, or by way of an operator (surgeon command) toggling a foot switch, hand switch, or voice control, for example. The software that controls the low frequency and high frequency can be executed via the computer controller 380 or equivalent computing device.

Figure 10:
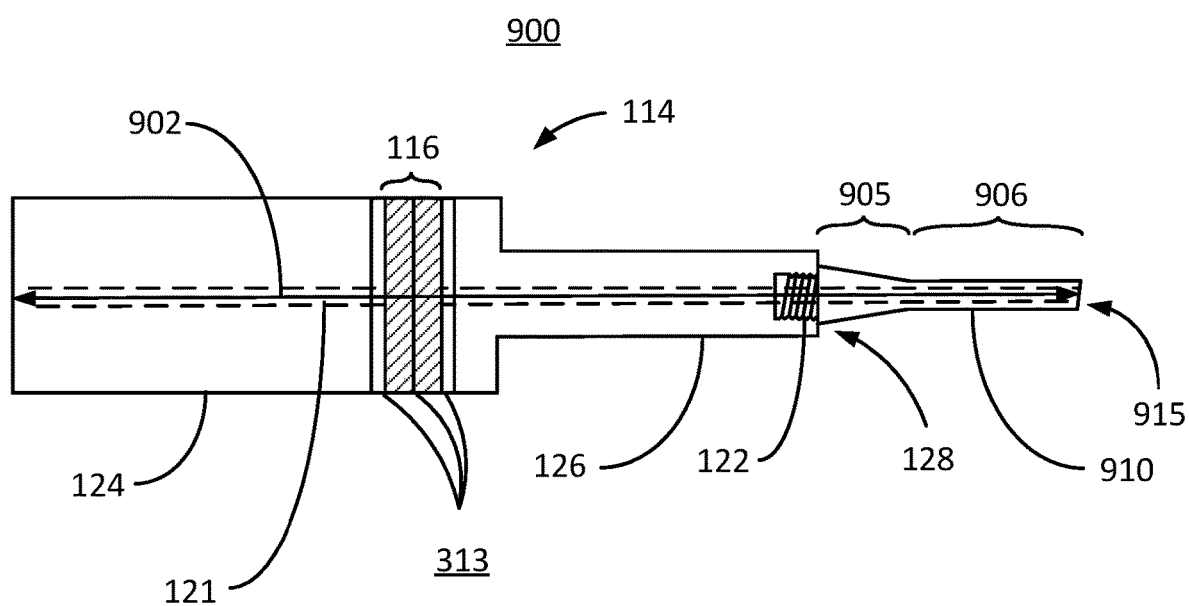
FIG. 10 illustratively depicts a line drawing of a phacoemulsification embodiment consistent with embodiments of the present invention.

FIG. 10 illustratively depicts a line drawing of a phacoemulsification embodiment consistent with embodiments of the present invention. As shown, the phacoemulsification handpiece 114 does not have a tapered region in the step horn 126. Rather, there is a tapered region 905 at the proximal end of the titanium needle 910. In this embodiment, the tapered region 905 is configured to control the node of minimum amplitude along the substantially cylindrical portion 906 of the needle 910. As with the tapered portion of the horn in the previous embodiment of FIGS. 8 and 9, a tapered mode of minimum amplitude can be designed to fall either within the tapered region 905 of the needle 910 or in the cylindrical step horn cylinder 126. Some embodiments envision the needle 910 being a unitary titanium element. For reference, a longitudinal axis 902 that extends from the back of the handpiece cylinder 124 to the free distal tip 915 is illustratively shown. The longitudinal axis 902 can equally be applied to the other phacoemulsification devices, such as 800, described herein.

Figure 11A:
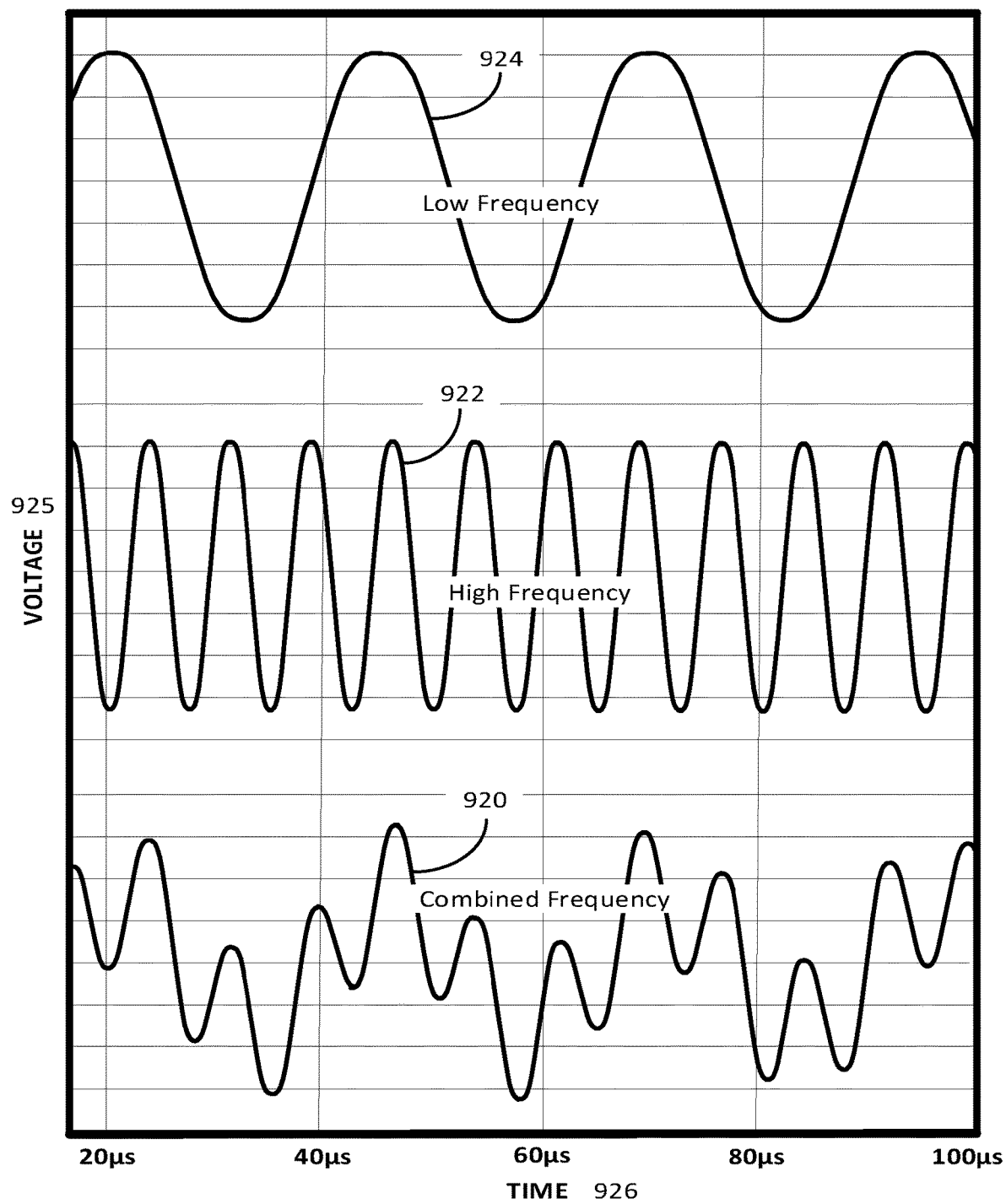
FIG. 11A illustrates superposition of a low frequency plot and a high frequency plot consistent with embodiments of the present invention.

FIG. 11A illustrates superposition of a low frequency plot and a high frequency plot consistent with embodiments of the present invention. More specifically, graphs of three frequency signals plotted with voltage 925 (ordinate) versus time 926 (abscissa) is shown. The low frequency signal 924 is added to the high frequency signal 922 to generate the combined frequency signal 920. As shown, the low frequency 924 and the high frequency 922 are each generated with essentially equal power, hence both have the essentially same amplitude. In this way, the combined frequency 920 is not dominated by either the low frequency 924 or the high frequency 922. Certain embodiments envision the low frequency 924 having higher power than the high frequency 922 thereby generating a situation where the low frequency 924 is essentially a carrier frequency (not shown) of the high frequency 922. Likewise, if the high frequency 922 is generated via a higher applied power than the low frequency 924, the high frequency 922 will have a more dominating effect on the combined frequency (not shown). Certain embodiments of the present invention envision the piezoelectric transducer apparatus 116/124 of the phacoemulsification handpiece 114 generating the two frequencies 922 and 924, as shown in FIG. 11B.

Figure 11B:
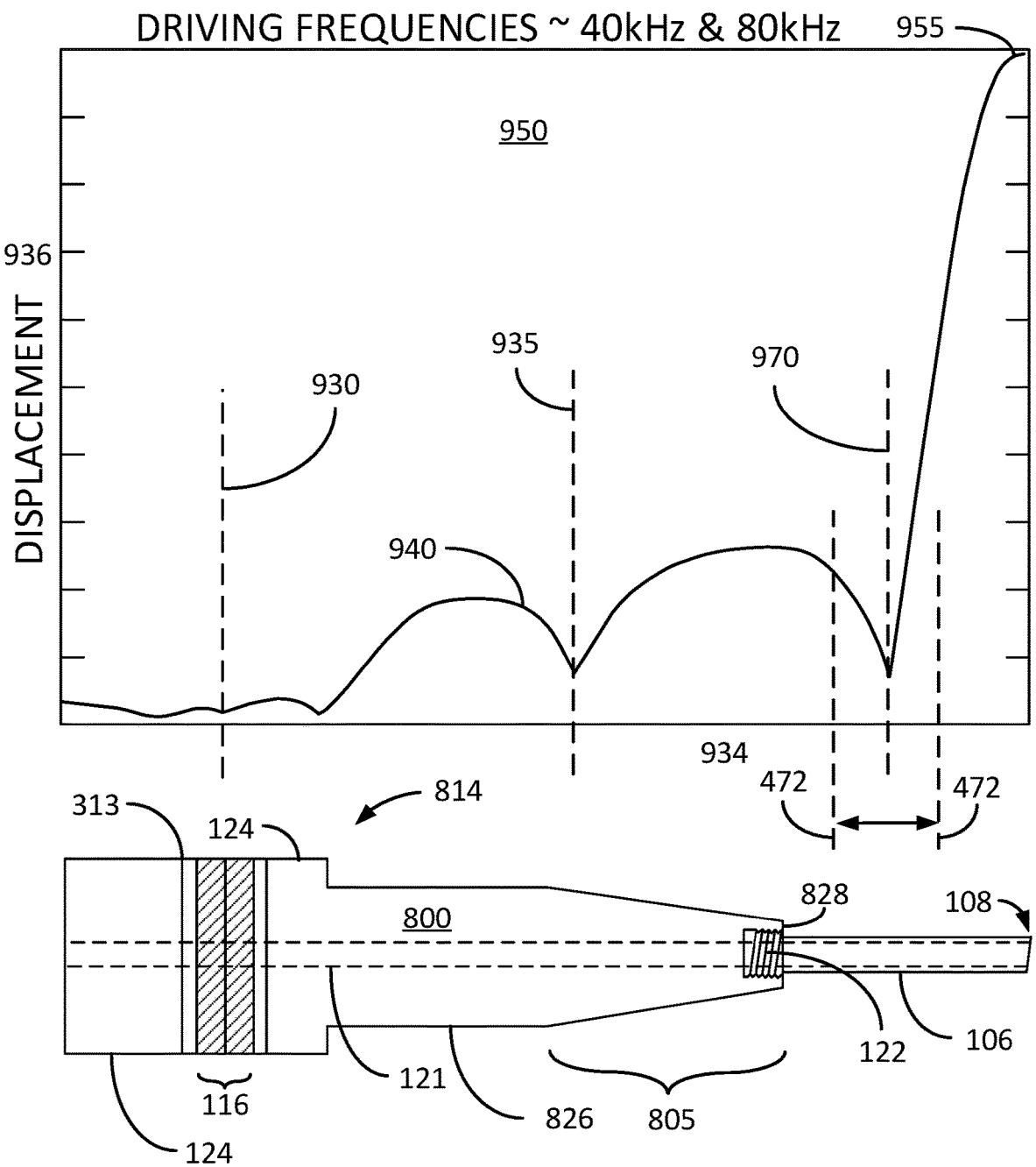
FIG. 11B is a plot of a standing wave at the combined frequencies with respect to a phacoemulsification device embodiment consistent with embodiments of the present invention.

FIG. 11B is a plot of a standing wave at the combined frequencies with respect to a phacoemulsification device embodiment 810 consistent with embodiments of the present invention. As shown, the vibration response graph/plot 950 is of a standing wave 940 of the combined two frequencies 922 and 924 resonating the phacoemulsification device 800. Here, the low frequency is approximately 40 kHz and the high frequency is approximately 80 kHz, however other certain embodiments envision the low frequency below 60 kHz and the high frequency being above 60 kHz. It is further envisioned that the standing wave 940 created by the high and low frequencies 922 and 924 is essentially a superposition of the high frequency standing wave 819 over the low frequency standing wave 817 (depicted in FIGS. 8 and 9). Accordingly, the displacement response plot 940 (i.e., the resonant displacement 936 of the phacoemulsification device 800 along the length 934 of the device 800) comprises a step horn semi-node of low amplitude 935 in the tapered section 805 and a single semi-node of low amplitude 970 along the length of the needle 106. Unlike the nodes of minimum amplitude 835 and 870 of FIG. 9, the semi-nodes of low amplitudes 935 and 970 do not have a near zero displacement of vibration on the device 800, rather they create a mere depression in the resonant response of the device 800. Accordingly, the needle 106 has a cool region 972 (depicted by the double arrow between the lines 972) that keeps the eye 101 from burning where the needle 106 interfaces the eye 101. As further shown, there is an antinode 955 approximately at the free distal tip 108.

Some embodiments of the present invention envision a surgeon/operator adjusting power to the phacoemulsification device 800 to drive one of the frequencies to dominate over the other. More specifically, certain embodiments envision a switch, a foot pedal, voice control, or some other input, to simultaneously increase power of the high frequency mode 922 while proportionally decreasing power to the low frequency mode 924, and vise-versa. Increasing power to the high frequency mode 922 (with a proportional decrease in power to the low frequency mode 924) could be accomplished in discrete intervals or optionally smoothly over an infinite range of power levels, or somewhere in between. In this way, the needle 106 can be made to more effectively cut cataractous material into fragments while minimizing cavitation with a "cool" needle 106. Decreasing power to the high frequency mode 922 while proportionally increasing power to the low frequency mode 924 can serve to emulsify the fragments for better aspiration through the aspiration pathway 121. Having both frequencies being used together provides certain benefits of more efficiently cutting and emulsifying fragments of cataractous eye material. When providing a surgeon with the opportunity to adjust the power of one frequency over another, maneuvering through a cataract surgery to remove cataracts can be accomplished more efficaciously. In short, in consideration that while lowering ultrasonic frequencies enhances cavitation but generates more heat, the higher frequencies increase fragmentation without increasing heat, the two frequencies can be combined in different proportions to best suit the situation. For example, driving the lower frequency with lower power and increasing power for the high frequency could help fragment harder cataract tissue when cutting is more important than most of the occasion. This can be done with purely longitudinal waves. By turning up or down the low frequency (and inversely proportionally forcing a down or up response to the high frequency), a surgeon is envisioned to have improved control.

Though embodiments described in conjunction with FIG. 11B are directed to phacoemulsification device 800 with the tapered region 805, other embodiments of a phacoemulsification device 100 with no such taper are considered. These vibration concepts can be used in conjunction with any number of different phacoemulsification devices without departing from the scope and spirit of the present invention.

With the present description in mind, some embodiments of the present invention therefore contemplate:

A surgical instrument 800 for a phacoemulsification procedure, the surgical instrument 800 comprising: a handpiece 814 that includes a piezoelectric transducer 116 and 124 and a step horn 126; a hollow titanium needle 106 having a free distal tip 108 and a supported end structure 122 that is attached to the handpiece 814, the supported end structure 122 includes external threads that mate with internal threads in the handpiece 814, the hollow titanium needle 106 having a substantially cylindrical portion 106 extending from the free distal tip 108 towards the step horn 126; a tapered section 805 in step horn 126, the step horn 126 is between the piezoelectric transducer 116/124 and the hollow titanium needle 106; and the piezoelectric transducer 116/124 configured to periodically vibrate the hollow titanium needle 106 at either a low mode (frequency) or a high mode (frequency), the substantially cylindrical portion devoid of a node of minimum amplitude at the low mode and the substantially cylindrical portion 106 possessing a single node of minimum amplitude 870 at the high mode.

The surgical instrument embodiment further envisioning wherein the low mode is below 60 kHz and the high mode is equal or above 60 kHz.

The surgical instrument embodiment further envisioning wherein the tapered section is selected from a group consisting of a geometry that is conical, elliptical, Gaussian, exponential, or Fourier.

The surgical instrument embodiment further envisioning wherein the piezoelectric transducer 116 is configured to switch between the high mode and the low mode by a surgeon command.

The surgical instrument embodiment further envisioning wherein the tapered section 805 extends approximately to the supported end structure 122.

The surgical instrument embodiment further envisioning wherein the piezoelectric transducer 116 is configured to switch automatically between the high mode and the low mode by a command received from the phaco machine controller 380.

The surgical instrument embodiment further envisioning wherein there is a single taper node of minimum amplitude 835 at the high mode along the tapered substantially cylindrical section of the needle and at the low mode along the tapered section.

The surgical instrument embodiment further envisioning wherein the free distal tip 108 is configured to periodically vibrate at a high amplitude in both the low mode and the high mode.

The surgical instrument embodiment further envisioning wherein the tapered section is integral with the headpiece.

The surgical instrument embodiment further envisioning wherein the piezoelectric transducer 116/124 is adapted to switch between the high mode and the low mode after a predetermined time interval.

Other embodiments contemplate a method to drive oscillations in a surgical instrument 800 during phacoemulsification, the method comprising: providing a handpiece 814 that includes a piezoelectric transducer 116/124 and a step horn 126, the step horn 126 possessing a tapered section 805 that tapers towards a distal handpiece end 828, a hollow titanium needle 106 having a free distal tip 108 and a supported end structure 122 that is attached to the distal handpiece end 828, the hollow titanium needle 106 possessing a length being defined along a longitudinal axis 902 of the hollow titanium needle 106; energizing the piezoelectric transducer 116/124 to periodically longitudinally expand and contract in at least two ultrasonic driving frequencies that rings the hollow titanium needle 106 with at least either a high ultrasonic standing wave 819 or a low ultrasonic standing wave 817; inserting the hollow titanium needle 106 in an eye 120; after the inserting step, energizing the piezoelectric transducer to drive the hollow titanium needle 106 at either the high ultrasonic standing wave 819 or the low ultrasonic standing wave 817, only the high ultrasonic standing possessing a node of minimum amplitude 870 along the length 854 of the hollow titanium needle 106.

The method embodiment further envisioning wherein the high and the low standing waves have a proximal node of minimum amplitude along the tapered section 835.

The method embodiment further envisioning wherein the high and the low standing waves have a distal anti-node of maximum amplitude 822 at the free distal tip 108.

The method further comprising switching the ultrasonic driving frequencies from ringing the hollow titanium needle 106 at the high ultrasonic standing wave 819 to the low ultrasonic standing wave 817 after a predetermined amount of time.

The method further comprising switching from the low ultrasonic standing wave 817 to the high ultrasonic standing wave 819 when the hollow titanium needle 106 becomes at least partially occluded and switching from the high ultrasonic standing wave 819 to the low ultrasonic standing wave 817 when the hollow titanium needle 106 is no longer partially occluded.

The method embodiment further envisioning wherein the low ultrasonic standing wave 817 is defined by a frequency below 60 kHz and the high ultrasonic standing wave 819 is defined by a frequency above 60 kHz.

The method embodiment further envisioning wherein the tapered section 805 is defined by a profile that is selected from a group consisting of a geometry that is conical, elliptical, Gaussian, exponential, or Fourier.

Yet another embodiment contemplates a phacoemulsification device comprising: a phacoemulsification device 800 possessing a handpiece 814 that tapers 805 to a tapered end 828, a hollow titanium needle 106 attached to the tapered end 828, the hollow titanium needle 106 having a substantially cylindrical portion that extends from approximately the tapered end 828 to a free distal tip 108; and a transducer 116/124 configured to drive the hollow titanium needle 106 with either a low ultrasonic standing wave 817 or a high ultrasonic standing wave 819, the high ultrasonic standing wave 819 having a single node of minimum amplitude 870 along the hollow titanium needle 106, the low ultrasonic standing wave 817 devoid of any node of minimum amplitude along the hollow titanium needle 106.

The phacoemulsification device embodiment further envisioning wherein the transducer 116 is configured to change between the low ultrasonic standing wave 817 and the high ultrasonic standing wave 819.

The phacoemulsification device embodiment further envisioning wherein the low ultrasonic standing wave 817 having a frequency of less than 60 kHz and the high ultrasonic standing wave 819 having a frequency of more than 60 kHz.

In a different embodiment, a phacoemulsification procedural instrument 800 is contemplated comprising: a handpiece 814 that includes a piezoelectric transducer 116/124; a hollow titanium needle 106 having a free distal tip 108 and a supported end structure 122 that is attached to the handpiece 814, the supported end structure 122 includes external threads that mate with internal threads in the handpiece 814, the hollow titanium needle 106 having a substantially cylindrical portion extending from the free distal tip towards 108 the handpiece 814; and the piezoelectric transducer 116 configured to periodically vibrate the hollow titanium needle 106 with a standing wave 940 defined by a high frequency mode 922 superimposed over a low frequency mode 924, the standing wave 940 defining a single semi-node of low amplitude 970 along the substantially cylindrical portion 106 and an anti-node of high amplitude 955 at the free distal tip 108.

The phacoemulsification procedural instrument 800 embodiment further envisioning wherein the low frequency mode 924 is below 60 kHz and the high frequency mode 922 is equal or above 60 kHz.

The phacoemulsification procedural instrument 800 embodiment further comprising a tapered section 805 between the piezoelectric transducer 116/124 and the substantially cylindrical portion of the needle 106.

The phacoemulsification procedural instrument 800 embodiment further envisioning wherein the piezoelectric transducer 116 is configured to be adjusted by a surgeon command to increase or decrease power of the high frequency mode 922 inversely to the low frequency mode 922.

The phacoemulsification procedural instrument 800 embodiment further envisioning wherein the tapered section 805 extends approximately to the supported end structure 122.

The phacoemulsification procedural instrument 800 embodiment further envisioning the piezoelectric transducer 116/124 configured to adjust power of the high frequency mode 922 inversely proportional to the low frequency mode 924 by a command received from the phaco machine controller 380.

The phacoemulsification procedural instrument 800 embodiment further envisioning wherein there is a single taper node of low amplitude 935 at along the tapered section 805.

The phacoemulsification procedural instrument 800 embodiment further envisioning wherein the low frequency mode 924 and the high frequency mode 922 both vibrate longitudinally along the hollow titanium needle 106.

The phacoemulsification procedural instrument 800 embodiment further envisioning wherein the tapered section 805 is selected from a group consisting of a geometry that is conical, elliptical, Gaussian, exponential, or Fourier.

The phacoemulsification procedural instrument 800 embodiment further envisioning wherein the piezoelectric transducer 116/124 is adapted to adjust power of the high frequency mode 922 inversely proportional to the low frequency mode 924.

Aspects of the present invention further contemplate a method to drive oscillations in a surgical instrument 800 during phacoemulsification, the phacoemulsification procedure method comprising: providing a handpiece 814 that includes a piezoelectric transducer arrangement 116/124, a hollow titanium needle 106 having a free distal tip 108 and a supported end structure 122 that is attached to the distal handpiece end 828, the hollow titanium needle 106 possessing a length being defined along a longitudinal axis 902 of the hollow titanium needle 106; energizing the piezoelectric transducer arrangement 116/124 to periodically longitudinally expand and contract in at least two simultaneously driving ultrasonic frequencies 920 made up of at least a high ultrasonic frequency 922 and a low ultrasonic frequency 924, the at least two simultaneously driving ultrasonic frequencies 920 ring the hollow titanium needle 106 with a standing wave 940 defined by at least a high ultrasonic standing wave 819 superimposed over a low ultrasonic standing wave 817; inserting the hollow titanium needle 106 in an eye 101; and after the inserting step, energizing the piezoelectric transducer 116/124 to drive the hollow titanium needle 106 at the simultaneously driving ultrasonic frequencies 920, the standing wave 940 defining a single semi-node of low amplitude 970 along the hollow titanium needle 106 and an anti-node of high amplitude 955 at the free distal tip 108.

The phacoemulsification procedure method embodiment further envisioning wherein the handpiece 114 further possesses a tapered section 805 that tapers towards a distal handpiece end 828.

The phacoemulsification procedure method embodiment further envisioning wherein the standing wave 940 has a proximal node of low amplitude 935 along the tapered section.

The phacoemulsification procedure method embodiment further envisioning wherein the anti-node of high amplitude 955 is a distal anti-node of maximum amplitude 955 at the free distal tip 108.

The phacoemulsification procedure method embodiment further comprising increasing power to the high frequency mode 922 while inversely decreasing the power to the low frequency mode 924, or decreasing the power to the high frequency mode 922 while inversely increasing the power to the low frequency mode 924.

The phacoemulsification procedure method embodiment further envisioning further comprising increasing the power to the high frequency mode 922 while inversely decreasing the power to the low frequency mode 924 when the hollow titanium needle 106 becomes at least partially occluded and switching from the high ultrasonic frequency mode 922 to the low ultrasonic frequency mode 924 when the hollow titanium needle 106 is no longer partially occluded.

The phacoemulsification procedure method embodiment further envisioning wherein the low ultrasonic frequency 924 is below 60 kHz and the high ultrasonic frequency 922 is above 60 kHz.

Other aspects of the present invention consider a hand-held surgical instrument comprising: a phacoemulsification device 800 possessing a handpiece 114, a hollow titanium needle 106 attached to the handpiece 114, the hollow titanium needle 106 having a substantially cylindrical portion that extends from approximately the handpiece 114 to a free distal tip 108; and a transducer configured to drive the hollow titanium needle 106 with at least two simultaneous driving frequencies 922 and 924 that define a standing wave 940 with a single semi-node of low amplitude 970 along the hollow titanium needle 106 and an anti-node of high amplitude 955 at the free distal tip 108.

The hand-held surgical instrument embodiment further envisioning wherein the transducer 116/124 is configured to increase power to the high frequency mode 922 while inversely decreasing the power to the low frequency mode 924, or decrease the power to the high frequency mode 922 while inversely increasing the power to the low frequency mode 924.

The hand-held surgical instrument embodiment further envisioning wherein at least two simultaneous driving frequencies 920 comprise a high ultrasonic frequency 922 of more than 60 kHz and a low ultrasonic frequency 924 of less than 60 kHz.

The above embodiments are not intended to limit the scope of the invention whatsoever because many more embodiments are easily conceived within the teachings and scope of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, though embodiments of the present invention describe modulating between a high ultrasonic frequency and an ultrasonic frequency, it is contemplated that multiple ultrasonic frequencies and high ultrasonic frequencies can be used while still maintaining substantially the same functionality without departing from the scope and spirit of the present invention. The specification and drawings are to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

It will be clear that the claimed invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the claimed invention disclosed and as defined in the appended claims. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. A surgical instrument comprising:
   a phacoemulsification device possessing a handpiece that includes a step horn with a tapered section that tapers towards a distal step horn end, a hollow titanium needle attached to the distal step horn end and extends to a free distal tip; and
   a transducer configured to drive the hollow titanium needle with at least two simultaneous driving frequencies that define a standing wave with a single semi-node of low amplitude along the hollow titanium needle and an anti-node of high amplitude at the free distal tip.

2. The surgical instrument of claim 1 wherein the transducer is configured to increase power to the high frequency mode while inversely decreasing the power to the low frequency mode, or decrease the power to the high frequency mode while inversely increasing the power to the low frequency mode.

3. The surgical instrument of claim 1 wherein at least two simultaneous driving frequencies comprise a high ultrasonic frequency of more than 60 kHz and a low ultrasonic frequency of less than 60 kHz.

4. The surgical instrument of claim 1 wherein the tapered section is selected from a group consisting of a geometry that is conical, elliptical, Gaussian, exponential, or Fourier.

5. The surgical instrument of claim 1 wherein power to the piezoelectric transducer is configured to be adjusted wherein one of the frequencies dominates over another.

6. The surgical instrument of claim 5 wherein power to the piezoelectric transducer is adjustable by either a switch, a foot pedal, or voice control.

7. The surgical instrument of claim 5 wherein power to the piezoelectric transducer is adjustable by either a switch, a foot pedal, or voice control.

8. The surgical instrument of claim 5 further comprising a vacuum pump that during a phacoemulsification procedure is adapted to withdraw ocular material from an eye through the hollow titanium needle at an established vacuum, a circuit is adapted to switch from an ultrasonic frequency to a high-ultrasonic frequency when an established vacuum increases and from the high-ultrasonic frequency to the ultrasonic frequency when the established vacuum is no longer increased.

9. The surgical instrument of claim 5 wherein a circuit is adapted to switch from an ultrasonic frequency to a high-ultrasonic frequency when the circuit senses an increased load from a particle engaged with the hollow titanium needle in a way that does not pass through the hollow titanium needle and back to the ultrasonic frequency when the particle is either no longer engaged or the load is no longer increased.

10. The surgical instrument of claim 5 further comprising an irrigation sleeve possessing an irrigation port through which irrigation fluid is configured to discharge inside of an eye at a flow rate during a phacoemulsification procedure, the irrigation sleeve enveloping a portion of the hollow titanium needle, a circuit adapted to switch from an ultrasonic frequency to a high-ultrasonic frequency when the flow rate decreases and from a high-ultrasonic frequency to the ultrasonic frequency when the flow rate is no longer decreased.

11. The surgical instrument of claim 1 wherein said transducer is configured to increase power to the high frequency mode while inversely decreasing the power to the low frequency mode via discrete power intervals.

12. The surgical instrument of claim 1 wherein said transducer is configured to increase power to the high frequency mode while inversely decreasing the power to the low frequency mode via an infinite range of power levels.

13. The surgical instrument of claim 1 wherein power to the piezoelectric transducer is adjustable by the rate of flow passing through the hollow tip.

14. The surgical instrument of claim 1 further comprising a circuit that is configured to switch from the transducer from an ultrasonic frequency to a high-ultrasonic frequency during a phacoemulsification procedure when a rate at which ocular material passes through the hollow titanium needle slows, the circuit is further adapted to switch back to the ultrasonic frequency from the high-ultrasonic frequency when the rate at which the ocular material passes through the hollow titanium needle is no longer slowed.

15. A surgical instrument comprising:
a phacoemulsification device possessing a handpiece that includes a step horn that extends to a distal step horn end, a hollow titanium needle attached to the distal step horn end, the hollow titanium needle extending to a free distal tip;
a transducer configured to drive the hollow titanium needle with at least two simultaneous driving frequencies that define a standing wave with a single semi-node of low amplitude along the hollow titanium needle and an anti-node of high amplitude at the free distal tip; and
a tapered region between the transducer and the free distal tip.

16. The surgical instrument of claim 15 wherein the hollow titanium needle includes the tapered region.

17. The surgical instrument of claim 15 were in the step horn includes the tapered region.

18. The surgical instrument of claim 15 wherein the tapered section is selected from a group consisting of a geometry that is conical, elliptical, Gaussian, exponential, or Fourier.

19. A surgical instrument comprising:
a phacoemulsification device possessing a handpiece that includes a step horn extending to a distal step horn end configured to attach to a hollow titanium needle, the hollow titanium needle extending to a free distal tip; and
a transducer configured to drive the hollow titanium needle with at least two simultaneous driving frequencies that define a standing wave with a single semi-node of low amplitude along the hollow titanium needle and an anti-node of high amplitude at the free distal tip.

20. The surgical instrument of claim 19 wherein the step horn includes a tapered section.

21. The surgical instrument of claim 19 wherein the hollow titanium needle includes a tapered section.

22. The surgical instrument of claim 19 wherein the at least two simultaneous driving frequencies are superimposed longitudinal waves.

23. The surgical instrument of claim 19 wherein the at least two simultaneous driving frequencies comprise a high ultrasonic frequency of more than 60 kHz and a low ultrasonic frequency of less than 60 kHz.

24. The surgical instrument of claim 19 wherein the transducer is configured to increase power to the high frequency mode while inversely decreasing the power to the low frequency mode, or decrease the power to the high frequency mode while inversely increasing the power to the low frequency mode.

25. The surgical instrument of claim 19 wherein the hollow titanium needle having a substantially cylindrical portion that extends from approximately the distal step horn end to a free distal tip.

26. The surgical instrument of claim 19 wherein said transducer is configured to increase power to the high frequency mode while inversely decreasing the power to the low frequency mode via either discrete power levels or over an infinite range of power levels.

* * * * *